US008580977B2

(12) United States Patent
Shen

(10) Patent No.: US 8,580,977 B2
(45) Date of Patent: Nov. 12, 2013

(54) TAUTOMYCETIN AND TAUTOMYCETIN ANALOG BIOSYNTHESIS

(75) Inventor: Ben Shen, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/101,624

(22) Filed: May 5, 2011

(65) Prior Publication Data

US 2012/0010282 A1    Jan. 12, 2012

Related U.S. Application Data

(60) Provisional application No. 61/361,807, filed on Jul. 6, 2010.

(51) Int. Cl.
*C07D 303/00*   (2006.01)
*C12P 17/04*    (2006.01)

(52) U.S. Cl.
USPC ..................................... 549/323; 435/126

(58) Field of Classification Search
USPC ..................................... 549/323; 435/126
See application file for complete search history.

(56) References Cited

U.S. PATENT DOCUMENTS

2011/0281942 A1   11/2011   Shen et al.

OTHER PUBLICATIONS

Oikawa et al. Tetrahedron Letters, vol. 38, Issue 45, Nov. 10, 1997, pp. 7897-7900.*
Alder, et al., "Tautomycetin and tautomycin suppress the growth of medullary thyroid cancer cells via inhibition of glycogen synthase kinase-3beta," *Mol. Cancer Ther.*, 8:914-20, 2009.
Cheng, et al., "A new antibiotic, tautomycin," *J. Antibiot.*, 40:907-9, 1987.
Cheng, et al., "The structure of tautomycin, a dialkylmaleic anhydride antibiotic," *J. Antibiot.*, 43:890-6, 1990.
Cheng, et al., "The structure of tautomycin, a dialkylmaleic anhydride antibiotic," *J. Antibiot.*, 43:809-19, 1990.
Choi, et al., "Isolation of the biosynthetic gene cluster for tautomycetin, a linear polyketide T cell-specific immunomodulator from *Streptomyces* sp. CK4412," *Microbiology*, 153:1095-102, 2007.
Colby, et al., "A new model of the tautomycin-PP1 complex that is not analogous to the corresponding okadaic acid structure," *Bioorg. Med. Chem. Lett.*, 13:1601-5, 2003.
Han, et al., "Tautomycetin as a novel immunosuppressant in transplantation," *Transplant. Proc.*, 35:547, 2003.
Hur, et al., "Identification of TmcN as a pathway-specific positive regulator of tautomycetin biosynthesis in *Streptomyces* sp. CK4412," *Microbiology*, 154:2912-9, 2008.
Ju, et al., "Functional characterization of ttmM unveils new tautomycin analogs and insight into tautomycin biosynthesis and activity," *Org. Lett.*, 11:1639-42, 2009.

Kelker, et al., "Crystal structures of protein phosphatase-1 bound to nodularin-R and tautomycin: a novel scaffold for structure-based drug design of serine/threonine phosphatase inhibitors," *J. Mol. Biol.*, 385:11-21, 2009.
Lee, et al., "Tautomycetin inhibits growth of colorectal cancer cells through p21cip/WAF1 induction via the extracellular signal-regulated kinase pathway," *Mol. Cancer Ther.*, 5:3222-31, 2006.
Li, et al., "Characterization of the tautomycetin biosynthetic gene cluster from *Streptomyces* griseochromogenes provides new insight into dialkylmaleic anhydride biosynthesis," *J. Nat. Prod.*, 72:450-9, 2009.
Li, et al., "Characterization of the tautomycin biosynthetic gene cluster from *Streptomyces* spiroverticillatus unveiling new insights into dialkylmaleic anhydride and polyketide biosynthesis," *J. Biol. Chem.*, 283:28607-17, 2008.
Liu, et al., "SHP2 is a target of the immunosuppressant tautomycetin," *Chem. Biol.*, 18:101-10, 2011.
Luo, et al., "Functional characterization of TtnD and TtnF, unveiling new insights into tautomycetin biosynthesis," *J. Am. Chem. Soc.*, 132:6663-71, 2010.
Luo, et al., "Protein phosphatase 1 regulates assembly and function of the beta-catenin degradation complex," *EMBO J.*, 26:1511-21, 2007.
MacKintosh, et al., "Cyanobacterial microcystin-LR is a potent and specific inhibitor of protein phosphatases 1 and 2A from both mammals and higher plants," *FEBS Lett.*, 264:197-92, 1990.
Mitsuhashi, et al., "Tautomycetin is a novel and specific inhibitor of serine/threonine protein phosphatase type 1, PP1," *Biochem. Biophys. Res. Commun.*, 21:328-31, 2001.
Mitsuhashi, et al., "Tautomycetin suppresses the TNFalpha/NF-kappaB pathway via inhibition of IKK activation," *Int. J. Oncol.*, 33:1027-35, 2008.
Mitsuhashi, et al., "Usage of tautomycetin, a novel inhibitor of protein phosphatase 1 (PP1), reveals that PP1 is a positive regulator of Raf-1 in vivo," *J. Biol. Chem.*, 278:82-8, 2003.
Nishiyama, et al., "Structure-activity relationship within a series of degradation products of tautomycin," *Biosci. Biotechnol. Biochem.*, 60:103-7, 1996.
Oikawa "Synthesis of specific protein phosphatase inhibitors, tautomycin and tautomycetin toward structure-activity relationship study," *Curr. Med. Chem.*, 9:2033-53, 2002.
Sheppeck, et al., "Total Synthesis of the Serine/Threonine-Specific Protein Phosphatase Inhibitor Tautomycin(1)," *J. Org. Chem.*, 62:387-98, 1997.
Shim, et al., "Immunosuppressive effects of tautomycetin in vivo and in vitro via T cell-specific apoptosis induction," *Proc. Natl. Acad. Sci. USA*, 99:10617-22, 2002.
Sugiyama, et al., "Molecular shape analysis and activity of tautomycin, a protein phosphatase inhibitor," *Bioorg. Med. Chem. Lett.*, 6:3-8, 1996.
Takai, et al., "Effects of modification of the hydrophobic C-1-C-16 segment of tautomycin on its affinity to type-1 and type-2A protein phosphatases," *Biochem. J.*, 350:81-8, 2000.
Takai, et al., "Inhibition of specific binding of okadaic acid to protein phosphatase 2A by microcystin-LR, calyculin-A and tautomycin: method of analysis of interactions of tight-binding ligands with target protein," *Biochem. J.*, 306:657-65, 1995.

(Continued)

*Primary Examiner* — Nizal Chandrakumar

(57) ABSTRACT

The present invention relates to the biosynthetic gene cluster for tautomycetin (TTN) produces tautomycetin. Also provided are engineered micro-organisms for the production of TTN and analogs thereof, as well as methods of screening for compounds for activity.

10 Claims, 7 Drawing Sheets

(56) References Cited

OTHER PUBLICATIONS

Zhang and Zhang, "PTP1B as a drug target: recent developments in PTP1B inhibitor discovery," *Drug Discov. Today*, 12:373-81, 2007.

Zhang, et al., "Salicylic acid based small molecule inhibitor for the oncogenic Src homology-2 domain containing protein tyrosine phosphatase-2 (SHP2).," *J. Med. Chem.*, 53:2482-93, 2010.
Office Action issued in co-pending U.S. Appl. No. 13/101,612, dated Nov. 5, 2012.

\* cited by examiner

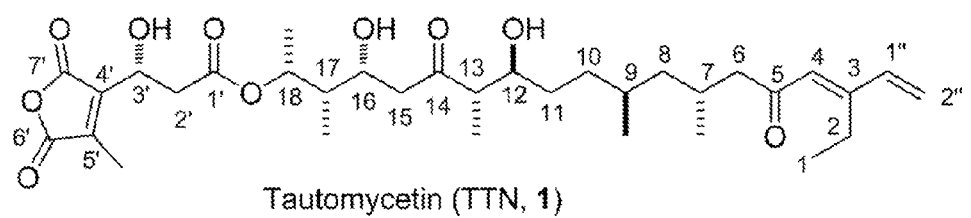
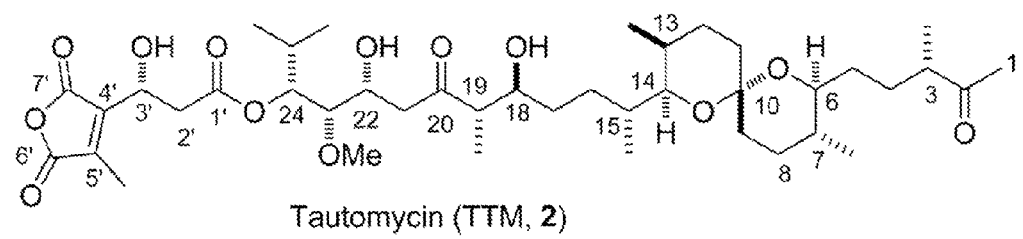
FIG. 1

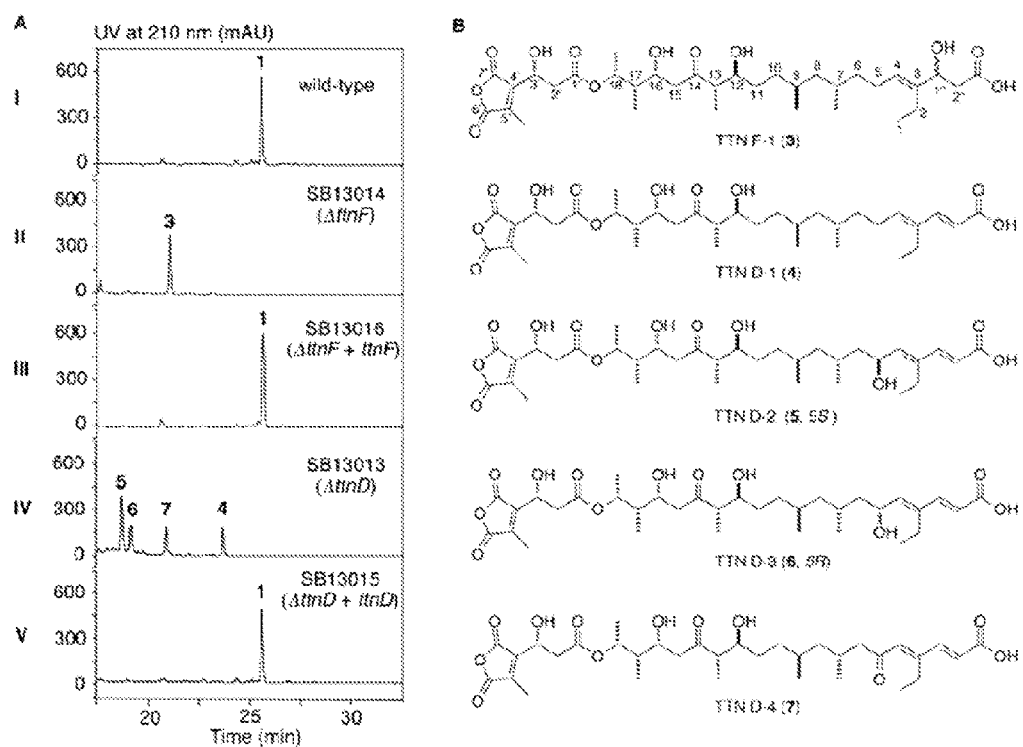
FIG. 2A-B

A
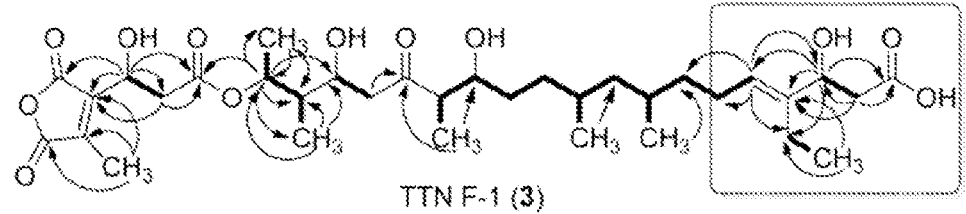
TTN F-1 (3)
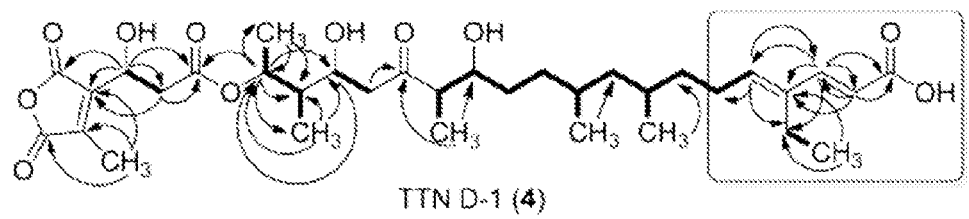
TTN D-1 (4)
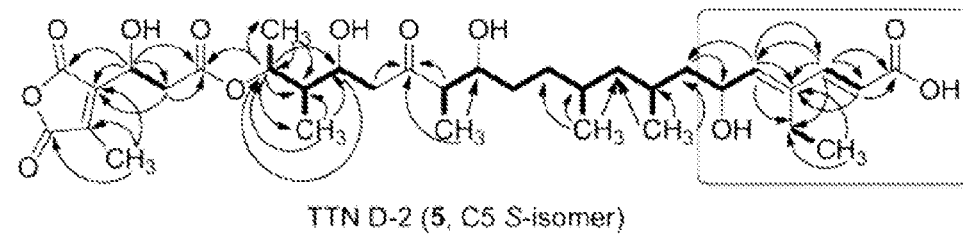
TTN D-2 (5, C5 S-isomer)
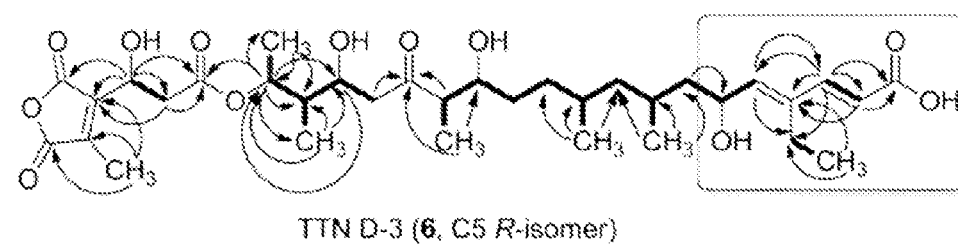
TTN D-3 (6, C5 R-isomer)
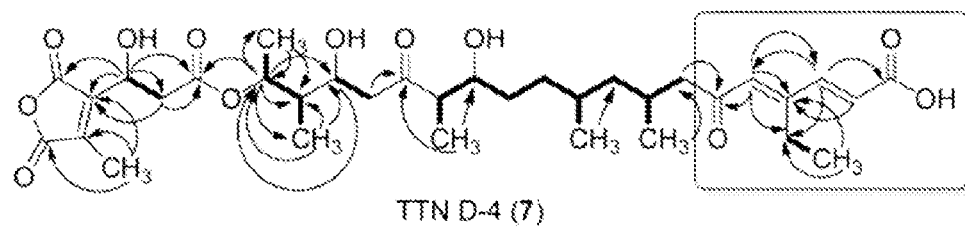
TTN D-4 (7)
—— $^1H$-$^1H$ COSY   ⌒ HMBC
FIG. 3A

B
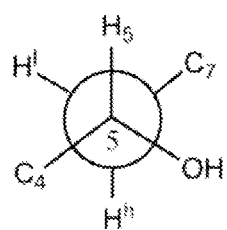 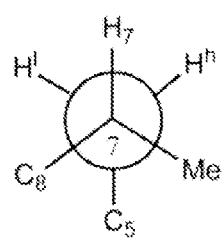 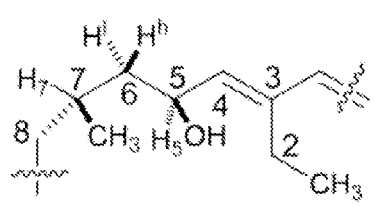
$^3J(H^h, H_5) = 9.0$ Hz
$^3J(H^l, H_5)$ = small
$^2J(H^h, C_5) = 6.8$ Hz
$^3J(H^l, C_4) = 1.3$ Hz
$^2J(H^l, C_5) = 1.2$ Hz
$^3J(H^h, H_7)$ = small
$^3J(H^l, H_7)$ = small
$^3J(H^l, Me) = 6.0$ Hz
C7-C3 fragment of TTN D-2 (5)
FIG. 3B

FIG. 5A-B

TAUTOMYCETIN AND TAUTOMYCETIN ANALOG BIOSYNTHESIS

The present application claims benefit of priority to U.S. Provisional Application Ser. No. 61/361,807, filed Jul. 6, 2010, the entire contents of which are hereby incorporated by reference.

This invention was made with government support under grant no. CA113297 awarded by the National Institutes of Health. The government has certain rights in the invention.

BACKGROUND OF THE INVENTION

I. Technical Field

The present invention relates generally to the fields of microbiology and bacterial genetics. More particularly, it concerns the biosynthetic pathway for tautomycetin (TTN) and its use to create TTN analogs.

II. Related Art

Tautomycetin (TTN, 1) and tautomycin (TTM, 2) (FIG. 1) are potent cell-permeable inhibitors of protein phosphatases (PPs) PP-1 and PP-2A and are recognized as potent inducers of apoptosis. TTN, first isolated from *Streptomyces griseochromogenes* (Cheng et al., 1989; Cheng et al., 1987), displays nearly a 40-fold preference for PP-1 inhibition over PP-2A and is the most selective PP-1 inhibitor reported to date (Mitsuhashi et al., 2001). The PP-1 selectivity of TTN likely plays a role in the agent's extraordinary immunosuppressive activity (Shim et al., 2002) and sharply contrasts the PP-2A selective inhibition by the natural product okadaic acid, another potent phosphatase inhibitor, making it a particularly useful tool (Bialogan and takai, 1988). Indeed, TTN has been instrumental in dissecting the role of PP-1 in the MEK-ERK pathway (Lee et al., 2006). TTM, isolated from *Streptomyces spiroverticillatus*, shares significant structural features with TTN, and yet displays only a weak preference for PP-1 inhibition relative to PP-2A (Mitsuhashi et al., 2001).

The inventor previously cloned and sequenced the biosynthetic gene clusters for both TTN and TTM (Li et al., 2009; Li et al., 2008). In the case of the highly selective PP-1 inhibitor TTN, the ttn biosynthetic gene cluster from *S. griseochromogenes* was characterized and its involvement in TTN biosynthesis confirmed by gene inactivation and complementation experiments (Li et al., 2009). The ttn cluster was localized to a 79-kb DNA region, consisting of 19 open reading frames that encode two modular type I polyketide synthases (TtnAB), one type II thioesterase (TtnH), eight proteins for dialkylmaleic anhydride biosynthesis (TtnKLMNOPRS), four tailoring enzymes (Tt-nCDFI), two regulatory proteins (TtnGQ), and one resistance protein (TtnJ). On the basis of functional assignments for each gene in the ttn cluster obtained from sequence analysis, the inventor formulated a model for biosynthesis of TTN that agrees well with previous feeding experiments, has been supported by in vivo gene inactivation experiments, and is supported by analogy to the recently reported ttm cluster. These findings set the stage to fully interrogate biosynthesis of TTN.

Of particular interest is the means by which the C222-C5 component (right hemisphere) is installed (FIG. 1). This component of TTN differs significantly from the corresponding right hemisphere of TTM and has been proposed as a crucial determinant dictating the greater PP-1 selectivity of TTN relative to TTM (Oikawa, 2002; Nishiyama et al., 1996; Sheppeck et al., 1997; Takai et al., 2000). This postulate has been substantiated by the recent crystal structure elucidation of PP-1 bound to TTM, although high-resolution structural information relating to PP-1 inhibition by TTN remains elusive (Kelker et al., 2009). Both TTN and TTM exist as equilibrating mixtures of anhydride and ring-opened diacids (Cheng et al., 1987; Cheng et al., 1990a; Cheng et al., 1990b); the PP-1-to-TTM crystal structure reveals that the diacid form of TTM is the active PP-1 inhibitor and implies, by analogy, that the diacid form of anhydride TTN is the species directly responsible for PP-1 inhibition (Kelker et al., 2009). The further understanding of the structure-function relationship of these compounds, as well as further analogs thereof, would be of considerable interest both from an academic standpoint as well as in the development of compounds for using in treating diseases such as cancer and autoimmune disfunction.

SUMMARY OF THE INVENTION

Thus, in accordance with the present invention, there is provided an isolated analog of tautomycetin (TTN) having the formula:

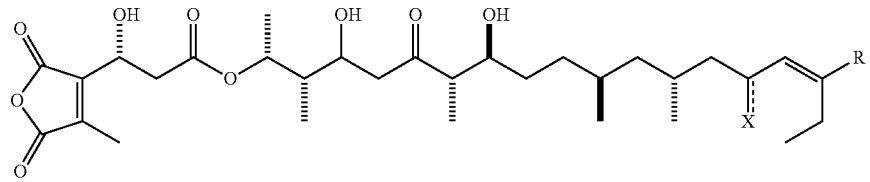

wherein X=O, OH or H, and R=(CH)$_2$COOH or CH(OH)CH$_2$COOH. Particular analogs include the following:

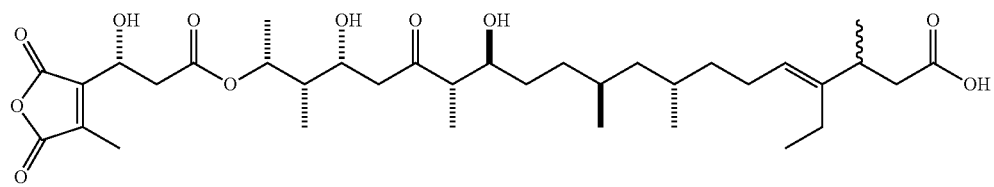

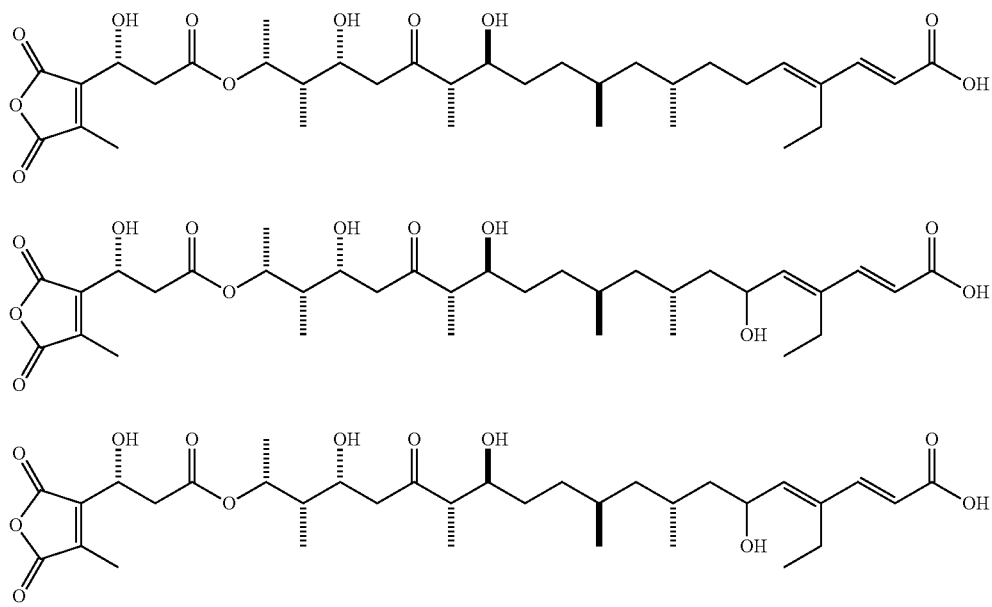

In another embodiment, there is provided a method of treating a subject with cancer comprising administering to said subject a compound as shown above. The cancer may be glioblastoma, medulloblastoma, astrocytoma, oligodendroglioma, ependymomas), lung, liver, spleen, kidney, pancreas, small intestine, blood cells, lymph node, colon, breast, endometrium, stomach, prostate, testicle, ovary, skin, head and neck, esophagus, bone marrow, or blood cancer. The cancer may be mtastatic, recurrent or multi-drug resistant. The subject may be a human. Administering may comprise systemic administration, such as intravenous, intraarterial or oral administration, or regional or local administration to a tumor site. The compound may be administered more than once. The method may further comprise providing to said subject a second therapy distinct from said compound. The second therapy may be chemotherapy, radiotherapy, or a combination thereof. The second therapy may be administered before or after said compound. The second therapy may be administered at the same time as said compound.

In still another embodiment, there is provided a method of treating a subject with an autoimmune disease comprising administering to said subject a compound as shown above. The autoimmune disease may be diabetes melitus, transplantation rejection, multiple sclerosis, premature ovarian failure, scleroderma, Sjogren's disease, systemic lupus erythematosus, vilelego, alopecia (baldness), polyglandular failure, Grave's disease, hypothyroidism, polymyositits, pemphigus, Crohn's disease, colititis, autoimmune hepatitis, hypopituitarism, myocardititis, Addison's disease, autoimmune skin diseases, uveititis, pernicious anemia, hypoparathyroidism, or rheumatoid arthritis. The autoimmune disease may be post-remission. The subject may be a human. Administering may comprise systemic administration, such as intravenous, intraarterial or oral administration. The compound may be administered more than once. The method may further comprise providing to said subject a second therapy distinct from said compound. The second therapy may be an anti-inflammatory therapy, such as a steroid or an NSAID. The second therapy may be administered before or after said compound. The second therapy may be administered at the same time as said compound.

In still a further embodiment, there is provided a method of producing a compound having the formula:

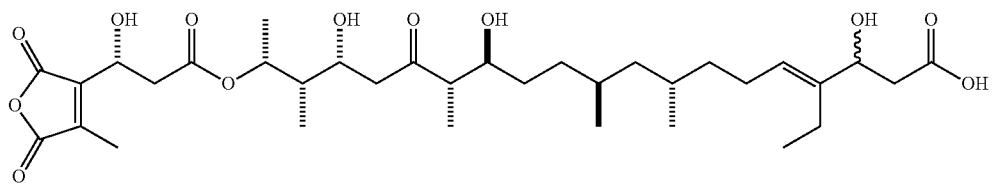 [SMILES: CC/C(=C\CC[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O)C(O)CC(=O)O]

comprising (a) providing a *Streptomyces* bacterium comprising an inactivating mutation in the ttnf gene; and (b) incubating said bacterium on conditions sufficient for a wild-type *Streptomyces* bacterium of the same species to produce tautomycetin.

An additional embodiment includes a method of producing a compound having the formula:

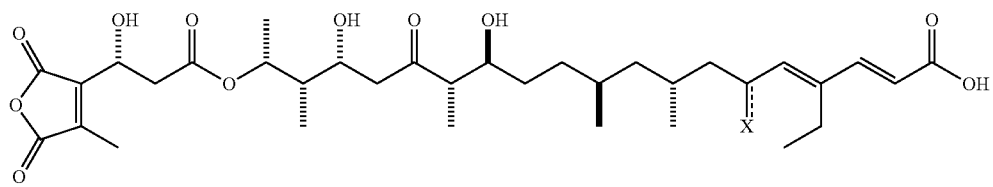

wherein X=O, OH or H, comprising (a) providing a *Streptomyces* bacterium comprising an inactivating mutation in the ttnd gene; and (b) incubating said bacterium on conditions sufficient for a wild-type *Streptomyces* bacterium of the same species to produce tautomycetin. The compound may have the formula:

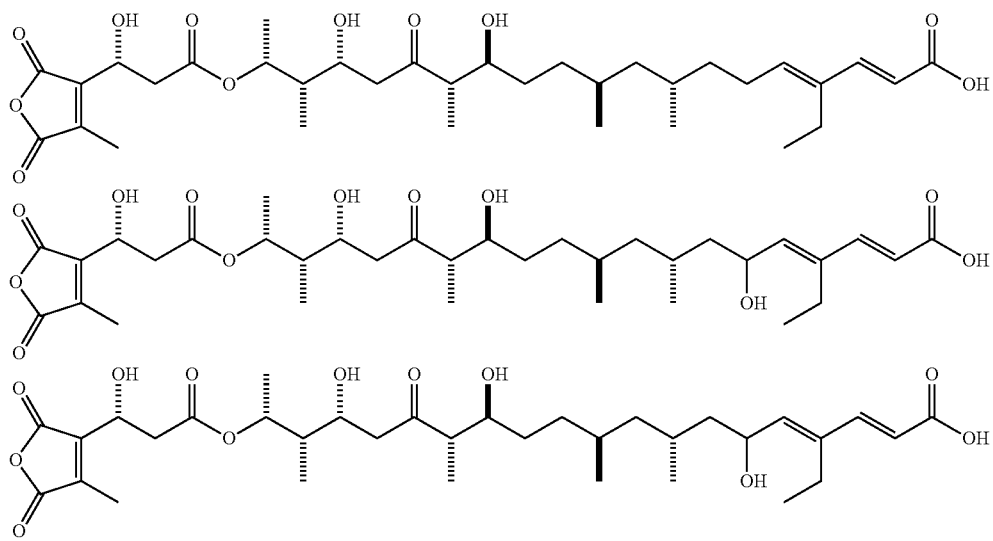

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1.
Structures of Tautomycetin (TTN, 1) and Tautomycin (TTM, 2).
FIGS. 2A-B.
TTN Biosynthetic Intermediates and Shunt Metabolites Accumulated in the ΔttnF and ΔttnD Mutant Strains SB13013 and SB13014.

(FIG. 2A) HPLC traces of metabolite profiles from *S. griseochromogenes* wild-type and mutant strains: (I) *S. griseochromogenes* wild-type; (II) SB13014 (ΔttnF mutant); (III) SB13016 (ΔttnF complemented); (IV) SB13013 (ΔttnD mutant); (V) SB13015 (ΔttnD complemented). Numbers above each peak correspond to TTN (1), TTN F-1 (3), TTN D-1 (4), TTN D-2 (5), TTN D-3 (6), and TTN D-4 (7).
(FIG. 2B) Structures of 3 from the ΔttnF mutant strain SB13013 and 4-7 from the ΔttnD mutant strain SB13014, as deduced on the basis of UV-vis, NMR, MS, and IR data.
FIGS. 3A-B.
$^1H$-$^1H$ COSY, HMBC HETLOC, gHSQMBC, and gDQ-COSY Analyses.
(FIG. 3A) Key $^1H$-$^1H$ COSY and HMBC correlations observed and applied to structure determination for TTN analogues 3-7.
(FIG. 3B) Determination of the 5-configuration at C5 of 5 on the basis of HETLOC, gHSQMBC, and gDQCOSY analyses.

(FIG. 5A) Restriction Map of the 140 kb DNA Region from *S. griseochromogenes* Harboring the Entire ttn Gene Cluster as Represented by Eight Overlapping Cosmids.

Solid black bar indicates sequenced DNA region. (FIG. 5B) Genetic organization of the ttn gene cluster. Proposed functions for individual orfs are coded with various patterns and summarized in Table 1, K, KpnI.

Figure 4:
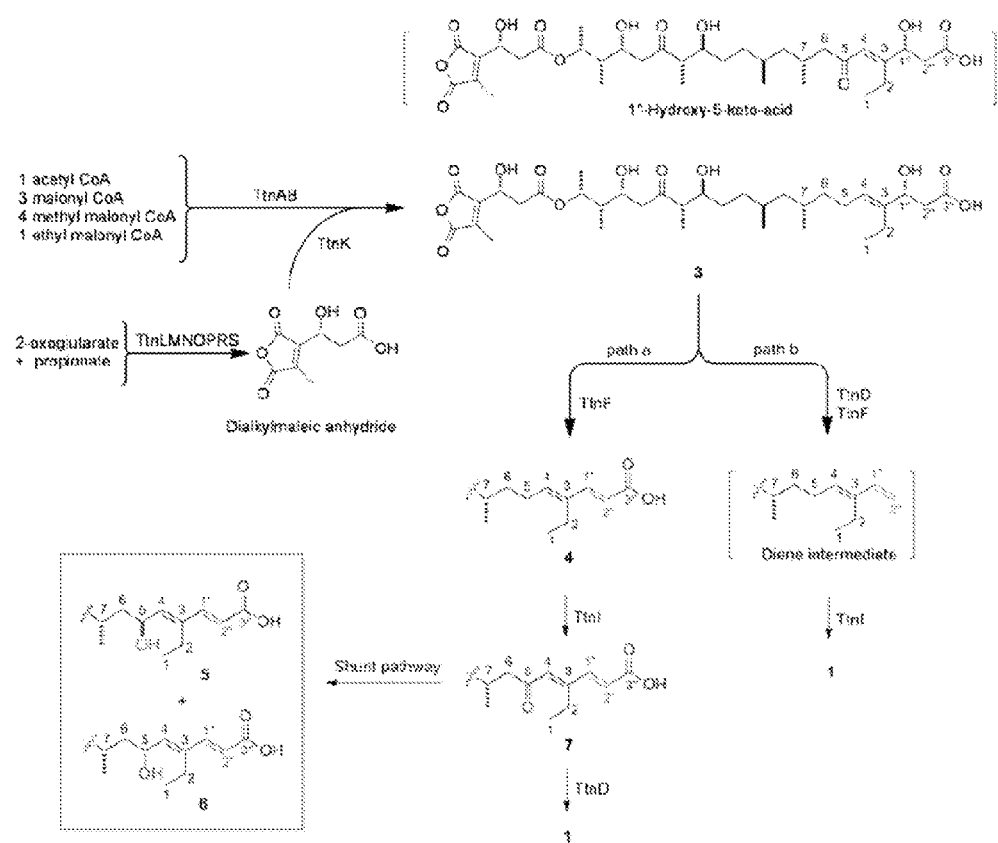
FIG. 4.
Proposed Biosynthesis of 1 Predicated on a Linear Biosynthetic Logic Leading to Intermediate 3 and Subsequent Processing by Tailoring Enzymes TtnD and TtnF.
Tailoring steps involving TtnF, TtnI, and TtnD and their ordering are assigned on the basis of metabolites 3-7 accumulated by ΔttnD and ΔttnF mutant strain SB13013 and SB13014s. We envision TtnI as a C5 oxidase on the basis of its similarity to cytochrome P450 hydroxylases. In proceeding from 3, path a invokes the sequential actions of TtnF, TtnI, and TtnD with 5 and 6 most likely derived by adventitious reduction of 7. Path b invokes coordinated activity by both TtnD and TtnF to produce a diene intermediate, which is subsequent oxidized at C5 by TtnI to afford 1. Molecular fragments not shown are identical to those of their putative precursor 3. The current studies disprove the intermediacy of 1"-hydroxy-5-keto acid in 1 biosynthesis proposed previously (Li et al., 2009).

Deduced Module and Domain Organization of TtnA and TtnB PKSs and a Linear Model for TTN Biosynthesis Featuring the TTN PKS Templated Assembly of the TTN Polyketide Backbone Featuring Various Starter and Extender Units, Coupling of the Dialkylmaleic Anhydride to the Elongating Polyketide Intermediate Prior its Reaching to Full Length, and Other Key Tailoring Steps.

The AT domains are coded with various patterns to highlight their substrate specificity, "X" marks domains predicted to be inactive, and dotted circles indicate intact domains whose activities appear to be unnecessary. AT, acyl transferase; ACP, acyl carrier protein; KS, ketosynthase; DH, dehydratase; KR, ketoreductase; ER, enoylreductase; TE, thioesterase.

DETAILED DESCRIPTION OF THE INVENTION

Here, the inventor reports that inactivation of two genes, ttnD and ttnF, in *S. griseochromogenes* abolishes production of TTN, instead leading to five new analogues, TTN F-1 (3), TTN D-1 (4), TTN D-2 (5), TTN D-3 (6), and TTN D-4 (7), all of which lack the terminal C1"-C2" olefin, a critical feature of the right hemisphere of TTN (FIGS. 2A-B). These findings support the proposed functions of TtnF and TtnD as a dehydratase and a decarboxylase, respectively (Li et al., 2009). Evaluation of the cytotoxicity and PP inhibitory activities of the new analogues highlights the importance of the C2"-C5 component in providing TTN with its ability to potently inhibit PP-1 in a highly selective fashion. These data significantly improve the understanding of TTN biosynthesis and PP inhibition by TTN, and provide for new molecules useful in conditions ranging from cancer to autoimmunity. These and other aspects of the invention are described in detail below.

I. Tautomycetin and Analogs Thereof

Tautomycetin (TTN), originally isolated from *Streptomyces griseochromogenes* in 1989, is structurally similar to tautomycin (TTM) (FIGS. 1A-B) (Cheng et al., 1989; Cheng et al., 1987). Both polyketides were initially described as antifungal antibiotics capable of inducing morphological changes in leukemia cells. More importantly, both compounds were found to specifically inhibit the protein phosphatases (PPs) PP1 and PP2A.3,4 PP1 and PP2A are two of the four major serine/threonine PPs that regulate an array of cellular processes including, but not limited to, cell cycle progression, gene expression, calcium transport, muscle contraction, glycogen metabolism, phototransduction, and neuronal signaling (Sakoff and McCluskey, 2004; Honkanen and Golden, 2002). Many human diseases are characterized by an altered interplay between phosphatases and kinases, and thus the selective inhibition of PP1 and PP2A has been proposed to be an attractive goal for rational anticancer drug design (McCluskey et al., 2002). For instance, TTN has been suggested as a potential drug for colorectal cancer because of its regulation of Raf-1 activity through inhibition of PP1 and PP2A in a cell-type-specific manner (Lee et al., 2006). PP1 and PP2A inhibition by TTM and TTN heightens interest in the possible application of combinatorial biosynthesis methods as an integral tool for the discovery of new therapeutics based on the anhydride-capped polyketide scaffold of TTM and TTN.

In contrast to other naturally occurring PP1 and PP2A inhibitors, such as okadaic acid (OA) (Bialojan and Takai, 1988), fostriecin (Roberge et al., 1994), cantharidin (Li and Casida, 1992), microcystin-LR (MacKintosh et al., 1990), and calyculin-A (Ishihara et al., 1989), TTM and TTN exhibit a high degree of PP1 selectivity. TTM inhibits PP1 and PP2A with $IC_{50}$ values of 22-32 nM while showing a slight preference for PP1 (MacKintosh et al., 1990; Colby et al., 2003; Oikawa, 2002; Sugiyama et al., 1996; Takai et al., 1995). Conversely, TTN preferentially inhibits PP1 by a factor of about 40-fold relative to PP2A ($IC_{50}$=1.6 nM for PP1 versus 62 nM for PP2A) (Mitsuhashi et al., 2001). By virtue of its high selectivity for PP1 inhibition, TTN represents not only an interesting drug lead but also a powerful biochemical tool with which to elucidate the roles of PP1 in various biological pathways.

Despite their similarities of structure and activity, TTN, but not TTM, has been identified as a potent immunosuppressor of activated T cells in organ transplantation (Shim et al., 2002). Inhibition of T cell proliferation by TTN was observed at concentrations 100-fold lower than those needed to achieve maximal inhibition by cyclosporine A (CsA). CsA and FK506 exert their pharmacological effects by binding to the immunophilins; the resulting complex binds to and inhibits the Ser/Thr phosphatase calcineurin albeit with potentially deleterious effects due to the physiological ubiquity of calcineurin (Flanagan et al., 1991; Bierer et al., 1990; Hong and Kahan, 2000). TTN exerts immunosuppressive activity in a manner completely different from those of CsA and FK506 by blocking tyrosine phosphorylation of intracellular signal mediators downstream of the Src tyrosine kinases in activated T cells. This leads to cell-specific apoptosis due to cleavage of Bcl-2, caspase-9, caspase-3, and poly(ADPribose) polymerase, but not caspase-1 (Shim et al., 2002; Chae et al., 2004). The activated T cell specificity of TTN thus suggests this unique polyketide as a significant lead in the search for immunosuppressive drugs superior to CsA and FK506.

The gross structure of TTN was deduced by chemical degradation and spectroscopic analysis (Cheng et al., 1990), and the relative and absolute stereochemistry was established by comparison of spectral data for degradation products of TTN with those of synthetic fragments (Dai et al., 1996). Both TTM and TTN exist as a tautomeric mixture consisting of two interconverting anhydride and diacid forms in approximately a 5:4 ratio under neutral conditions (Cheng et al. 1987; Cheng et al., 1990a; Cheng et al., 1990b). Since the major structural differences between TTM and TTN reside in the region distal to the dialkylmaleic anhydride, it has been proposed that these differences might be responsible for variations in their PP1 selectivity (Oikawa, 2002; Nishiyama et al., 1996; Sheppeck et al., 1997; Takai et al., 2000).

The inventor has now described analogs of TTN designated herein as TTN F-1 (3), TTN D-1 (4), TTN D-2 (5), TTN D-3

(6), and TTN D-4 (7). These analogs were created by inactivating the ttnf (F-1) and ttnd (D-1 to D-4) genes. These genes encode L-carnitine dehydratase and UbiD family decarboxylase enzymes, respectively. Each of these analogs is modified, with respect to TTN, at the right end of the molecule, where TTN has a terminal methylene group, and the analogs each have a terminal carboxy group with four of the five also being changed in the carbonyl group at C5. A generic structure for these molecules is shown below:

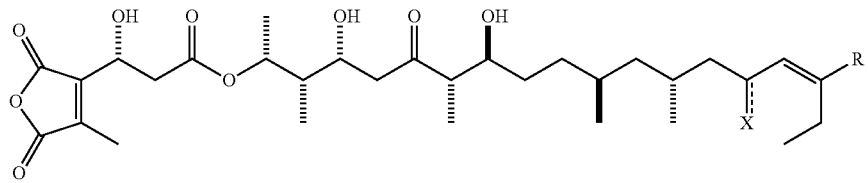

wherein X is O, OH or H, and R is $(CH_2)$—COOH or $CH(OH)CH_2$—COOH.

II. Characterization of the TTN Gene Cluster

Previously, the inventor reported the cloning and sequencing of the ttn gene cluster including a determination of its boundaries, along with the development of an expedient genetic system for S. griseochromogenes (Li et al., 2009). The bioinformatics analysis of the ttn cluster and a proposal for TTN biosynthesis were also presented along with the genetic characterization of the TTN pathway to support the proposed pathway (Li et al., 2009). Integral to this work was the elucidation, enabled by accurate assignment of the ttn cluster boundaries, of all genes responsible for dialkylmaleic anhydride biosynthesis. This report, combined with previous work on the ttm cluster, now enables rapid access to their biosynthetic gene cluster as well as genome mining of microorganisms for new dialkylmaleic anhydridecontaining natural products. A ΔttnM mutant was prepared, which produced the C-32 deshydroxy analogue TTN M-1.

A. Cloning and Sequencing

Figure 5:
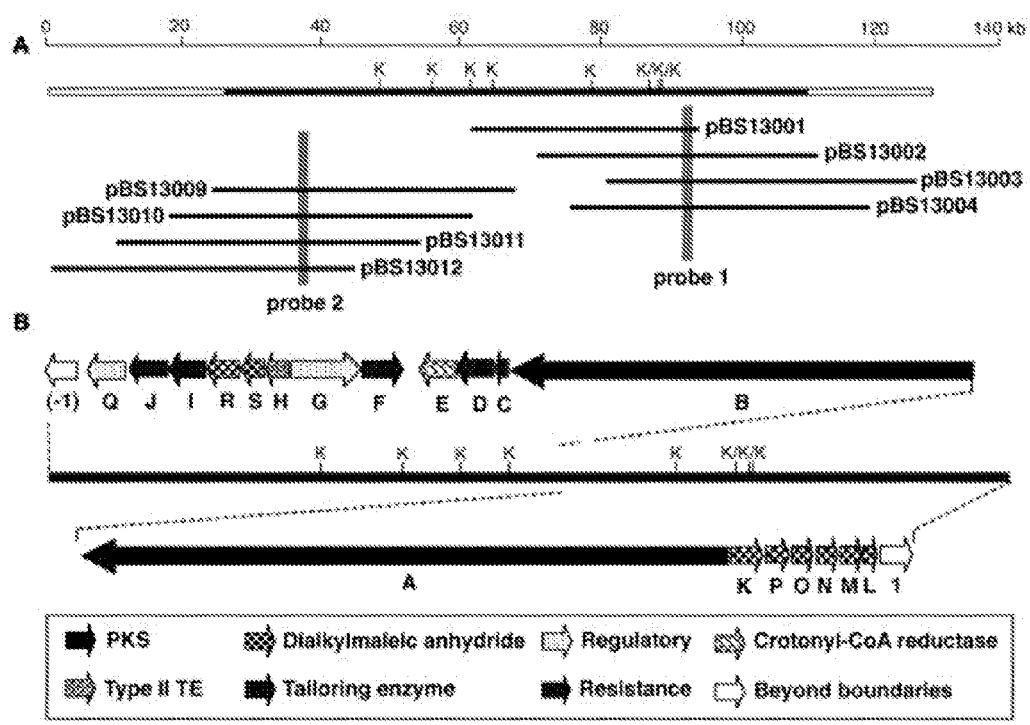
FIGS. 5A-B.

PCR and Southern analyses of which confirmed that the two loci, identified with probes 1 and 2, respectively, overlap (FIG. 5A). A total of 125 kb continuous DNA region was finally localized, 79 kb of which was ultimately sequenced on both strands. The overall G+C content for the sequenced region was 71.6%. The sequence was deposited in GenBank database under the accession number EU035755. Twenty-one complete open reading frames (orfs) were identified, among which 19 were designated as ttn genes (FIG. 5B). Corresponding homologues and the proposed function of each ttn gene product are summarized in Table 1. The deduced gene products include two large PKSs composed of a total of 10 modules, eight enzymes involved in dialkylmaleic anhydride biosynthesis, four tailoring enzymes, two regulatory proteins, and one resistance protein. While this work was in progress, a partial ttn cluster from Streptomyces sp. CK4412 was reported, which included 14 (i.e., spanning from ttnG to orf1) of the 21 orfs reported here; the cluster boundaries however were not determined (Choi et al., 2007). While not identical, the two clusters are highly homologous with protein amino acid sequences ranging from 97% to 99% identity.

TABLE 1

Deduced Functions of Open Reading Frames n the tautomycetin Biosynthetic Gene Cluster

| Gene | Size[a] | Proposed Function | Homologue[b] | Identity %/similarity % |
|---|---|---|---|---|
| orf(−1) | 262 | Transposase | MUL_2441 (YP_906264) | 32/42 |
| | | Upstream boundary of the ttn cluster | | |
| ttnQ | 472 | Transciptional activator | StaR (BAC55205) | 13/19 |
| ttnJ | 560 | Multidrug transporter | RHA1_ro04399 (YP_704343) | 49/53 |
| ttnI | 449 | Cytochrome P450 | EryF (1Z8Q_A) | 30/43 |
| ttnR | 470 | Dehydratase | PrpD (2HP3_A) | 24/38 |
| ttnS | 272 | Unknown | PFL_4035 (YP_261132) | 27/39 |
| ttnH | 259 | Thioesterase | PiKAV (AAC69333) | 42/53 |
| ttnG | 926 | Regulatory protein | ThcG (AAD28307) | 33/46 |
| ttnF | 505 | L-carnitine dehydratase | caiB (1XK7_B) | 12/24 |
| ttnE | 444 | Crotonyl-CoA reductase | CCr (AAA92890) | 75/84 |
| ttnD | 485 | UbiD family decarboxylases | UbiD (21DB_A) | 24/36 |
| ttnC | 209 | Flavoprotein decarboxylase | VdcB (AAD28781) | 57/71 |
| ttnB | 7576 | PKS modules 6-9 | | |
| ttnA | 9528 | PKS loading module and modules 1-5 | | |
| ttnK | 465 | Esterase | PnbA (1QE3_A) | 29/44 |
| ttnP | 383 | CoA transferase | CaiB (1XVV_A) | 24/41 |
| ttnO | 309 | Citryl CoA lyase | Mtb CitE (1Z6K_A) | 24/37 |
| ttnN | 363 | Unknown | EhPf (AAN40895) | 37/52 |
| ttnM | 339 | Hydroxylase | Plav_0577 (YP_001411857) | 29/42 |
| ttnL | 185 | Unknown | Ybhb (1FUX_A) | 25/33 |
| | | Downstream boundary of the ttn cluster | | |
| orf1 | 507 | Polyprenyl phospho-mannosyltransferase | MppI (AAU34200) | 32/48 |

[a]Numbers are in amino acids.
[b]Given n parentheses are NCBI accession numbers.

The ttn gene cluster boundaries were defined by combining bioinformatics analysis and gene inactivation (FIG. 5B). For the upstream boundary, orf(−1) encodes a putative transposase. Given the improbable role of a transposase during TTN biosynthesis, orf(−1) most likely lies beyond the ttn cluster. Immediately downstream of orf(−1) is a putative regulatory gene, ttnQ. Inactivation of ttnQ, affording the mutant strain SB13001, completely abolished TTN production, establishing its indispensability for TTM biosynthesis. For the downstream boundary, orf1 encodes a putative polyprenyl phosphomannosyltransferase. Inactivation of orf1, affording mutant strain SB13002, had little impact on TTN production, excluding the involvement of orf1 in TTN biosynthesis. Immediately upstream of orf1 is ttnL, a homologue of ttmL that has been confirmed to be essential for dialkylmaleic anhydride biosynthesis, hence essential for TTN biosynthesis (Li et al., 2008).

B. Assignment of Gene Function

Figure 6:
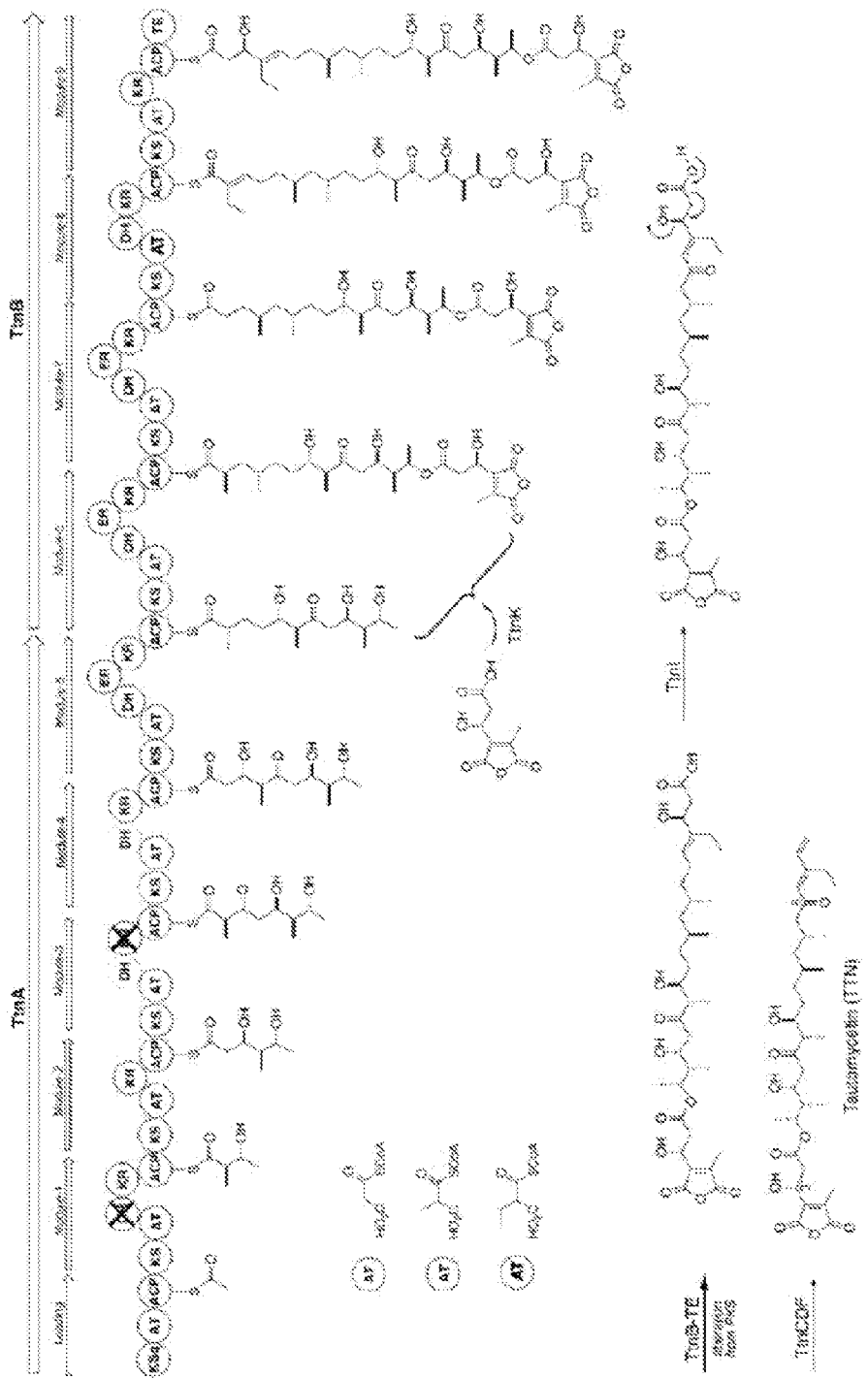
FIG. 6.

Two large orfs, ttnA and ttnB, that encode modular type I PKSs responsible were identified within the ttn cluster (FIGS. 5B and 6). The ttnA gene encodes the loading module and extension modules 1-5, whereas ttnB encodes extension modules 6-9 and has a C-terminal thioesterase domain for release of the full-length polyketide chain. Together, the TTN PKS of TtnA and TtnB consists of one loading module and nine extension modules and catalyzes nine rounds of decarboxylative condensation, using one malonyl CoA as a starter unit (loading module) and four malonyl CoA (modules 2, 4, 7, and 9), four methylmalonyl CoA (modules 1, 3, 5, and 6), and one ethylmalonyl CoA (module 8) as extender units, for initiation, elongation, and termination of the biosynthesis of the polyketide backbone of TTN (FIG. 6).

Domain functions were deduced by sequence homology to known PKS domains (Staunton and Weissman, 2001). The loading module contains a mutated ketosynthase (KSq), an acyltransferase (AT), and an acyl carrier protein (ACP) domain, and each of the nine extension modules is minimally characterized by ketosynthase (KS), AT, and ACP domains. All KS domains contain the CHH catalytic triad required for the decarboxylative condensation reaction. All the ACP domains feature the highly conserved signature motif of DSL, in which the serine residue acts as the site for 4'-phosphopantatheinylation, a post-translational modification essential for polyketide biosynthesis by converting the apo-ACPs into the functional holo-ACPs. The choice of the loading module and the extender unit is dictated by the corresponding AT domains, for which the specificity is predicted on the basis of sequence comparison with ATs of known substrates.

The nine extension modules are also characterized with additional domains such as ketoreductase (KR), dehydratase (DH), and enoylreductase (ER) domains, the presence of which accounts for the reductive modification of the β-keto group of the growing polyketide intermediate during each cycle of elongation. Functional KR domains, featuring the conserved consensus sequence GxGxxGxxA associated with NADP(H) binding, are found for all extension modules, except for KR in extender module 3, which contains a 16-amino acid deletion in the catalytic domain and, therefore, is inactive. Functional DH domains, containing the conserved consensus sequence HxxxGxxxxP, are identified for modules 5, 6, 7, and 8, excluding the DH domain in module 1, which contains a YxxxGxxxxP motif and, therefore, is inactive. In addition, intact DH domains are also present in extension modules 3 and 4, although their activities appear to be unnecessary in these modules. Finally, functional ER domains, having the conserved sequence GxGxAAxxxA, are predicted for modules 5, 6, and 7 (FIG. 6).

The TE domain at the C-terminus of TtnB terminates polyketide biosynthesis by liberating the full-length polyketide intermediate from the TTN PKS biosynthetic machinery (FIG. 6). Finally, in addition to the chain-terminating TE domain embedded within TtnB, a discrete type II TE (TEII), TtnH, remote from TtnA and TtnB within the ttn gene cluster, was also identified. TtnH may serve as an "editing" enzyme for mis-primed or stalled TtnA or TtnB PKS during polyketide chain elongation.

To support the predicted PKS function, ttnA was inactivated by using the PCR targeting strategies. Cosmid pBS13014, in which a 422 by DNA region within the ttnA gene was replaced with the aac(3)IV/oriT cassette, as introduced into S. griseochromogenes. Apramycin-resistant and kanamycin-sensitive exconjugants were selected as double crossover recombinant mutants, named SB13003, for which the desired ΔttnA genotype was confirmed by PCR and Southern blot analysis. Fermentation of SB13003, with the wild-type strain as a positive control, followed by extraction and HPLC analysis revealed that inactivation of ttnA completely abolished TTN production, consistent with the indispensable role proposed for TtnA in TTN biosynthesis.

Comparison of the TTM and TTN biosynthetic gene clusters revealed eight conserved enzymes, TtnKLMNOPRS, strongly supporting the involvement of these genes in dialkylmaleic anhydride moiety biosynthesis (Li et al., 2008). These conserved orfs include (i) TtmO/TtnO, a putative citryl-CoA lyase; (ii) TtmP/TtnP, a putative CoA transferase; (iii) TtmR/TtnR, a putative dehydratase; (iv) TtmM/TtnM, a putative hydroxylase; (v) TtmK/TtnK, a putative esterase; (vi) TtmS/TtnS, a putative cyclase; (vii) TtmL/TtnL, a phosphatidylethanolamine-binding protein; and (viii) TtmN/TtnN, an apparently conserved hypothetical protein. The coordination of these enzymatic activities for biosynthesis of the dialkylmaleic anhydride moiety is postulated.

Selected genes (ttnM, ttnP, ttnR, and ttnS) were next inactivated to investigate their roles in dialkylmaleic anhydride, hence TTN biosynthesis. In each case, the target gene was replaced in vitro by the aac(3)IV/oriT cassette using the PCR targeting strategies, yielding a mutated cosmid. Upon introduction of the mutated cosmids into wild-type S. griseochromogenes, apramycin-resistant and kanamycin-sensitive double crossover recombinant strains were selected, for which the desired mutant genotypes were finally confirmed by PCR and Southern blot analyses. Assigned names for each mutant strain are SB13004 (ΔttnM), SB13005 (AttnP), SB13006 (ΔttnR), and SB13007 (ΔttnS), respectively. Additionally, genetic complementation experiments were carried out to eliminate the possibility of polar effects. Plasmids pBS13017, pBS13018, and pBS13019, containing intact ttnM, ttnP, and ttnR genes under the control of ErmE* promoter, were introduced into SB13004, SB13005, and SB13006, yielding SB13009, SB13010, and SB13011, respectively.

These recombinant strains were fermented alongside the wild-type strain as a positive control, and TTN production was examined by HPLC analysis of the fermentation extracts. All four gene inactivation mutant strains failed to produce TTN, firmly establishing the essential roles these genes play in TTN biosynthesis. Moreover, under no circumstances were TTN intermediates detected in the SB13005 (AttnP), SB13006 (ΔttnR), or SB13007 (ΔttnS) mutant strain, consistent with the proposed critical functions of ttnP, ttnR, or ttnS in dialkylmaleic anhydride biosynthesis. TTN production was partially restored upon expression of a functional copy of the targeted gene in trans position, as exemplified by ttnP (pBS13022) and ttnR (pBS13023) to SB13005 (AttnP) and SB13006 (ΔttnR), respectively, to approximately 60% (SB13010) and 80% (SB13011) of the levels observed for the wild-type strain. The tmcD gene, the homologue of ttnP from the recently reported partial ttn cluster from S. sp. CK4412, has also been inactivated. The resultant ΔtmcD mutant strain also abolished TTN production, although no in vivo complementation to ΔtmcD was reported (Choi et al., 2007). In contrast, the SB13004 (ΔttnM) mutant strain accumulated four new compounds, with TTN M-1 being the predominant product. Introduction of the ttnM expression construct (pBS13021) into SB13004 partially restored TTN production to approximately 30% (SB13009) of the level seen for the wild-type strain with concomitant disappearance of the four new compounds. The latter result suggests that TtnM-mediated oxidation likely precedes convergence of the dialkylmaleic anhydride and polyketide halves of TTN. This is contrary to earlier postulates invoking TtnMmediated oxidation as the last step in TTN biosynthesis (FIG. 6) (Choi et al., 2007).

The identity of TTN produced by the *S. griseochromogenes* wild-type and recombinant strains was confirmed by MS and $^1$H and $^{13}$C NMR analysis; all spectra were identical to those of authentic TTN. The four new compounds produced by SB13004 were found to have UV-vis spectra identical to that of TTN, suggesting they all contain the dialkylmaleic anhydride moiety. The dominant compound, TTN M-1, was isolated, and its structure established by MS, UV-vis, $^1$H NMR, $^{13}$C NMR, and other 2D NMR methods as that of C3' deshydroxy-TTN. The three minor products of SB13004 fermentation were analyzed by HLPC-MS. Molecular weights for TTN M-2, TTN M-3, and TTN M-4 were found to be 576.4, 606.4, and 606.4 amu, respectively, but detailed structural elucidation was not pursued in the current study due to their minute production titers.

Compared to the nascent polyketide chain released by the TtnB terminal TE domain, the mature polyketide moiety of TTN has the following two varying functionalities: (i) a carbonyl group at C-5 position and (ii) the terminal diene structure. While TtnI (a cytochrome P450 hydroxylase) serves as a candidate for C-5 oxidation, the terminal diene structure calls for the nascent polyketide chain to undergo decarboxylation and dehydration upon release from TtnB. The latter are probably catalyzed by TtnC (a putative flavoprotein decarboxylase) or TtnD (a putative UbiD family decarboxylases) and TtnF (a putative L-carnitine dehydratase), respectively. The exact timing of carbonyl group formation, decarboxylation, and dehydration, however, needs to be determined by further experiments.

Regulatory and resistance proteins have also been unveiled upon sequencing the complete ttn cluster. The two regulatory genes identified within the ttn cluster are ttnG, which codes for a protein with 33% identity to the regulatory protein ThcG (AAD28307) from *Rhodococcus erythropolis*, and ttnQ, which codes for a protein with 41% identity to S are DRAFT_1231 (ZP_01648842) from *Salinispora arenicola* CNS205. Both TtnG and TtnQ belong to the LuxR family of transcription factors with the classical LuxR helix-turn-helix (HTH) motif proximal to each protein's C-terminus. Typically activated for DNA binding through associations with autoinducers such as N-(3-oxohexanoyl)-L-homoserine lactone, the LuxR homologues TtnG and TtnQ are intriguing since both lack an N-terminal autoinducer binding domain (Sitnikov et al., 1996). Additionally, TtnG contains a TTA leucine codon suggesting a possible dependence on bldA, the structural gene of tRNA$^{UUA}$ (Leskiw et al., 1993).

Identification of TtnG and TtnQ as regulatory protein candidates may have a bearing on metabolic engineering efforts to improve TTN titers. As described in the determination of the cluster boundary section, inactivation of ttnQ, affording mutant strain SB13001, completely abolished TTN production, a finding that agrees with TtnQ being a positive regulator. TTN production was partially restored to approximately 70% (SB13008) of the level seen for the wild-type strain upon introduction of the ttnQ expression construct (pBS13020) into SB13001. Similarly, tmcN, the homologue of ttnG from the recently appearing partial ttn cluster from S. sp. CK4412, has also been inactivated. The resultant ΔΔtmcN mutant strain completely lost its ability to produce TTN, as would be expected for a pathway-specific positive regulator (Hur et al., 2008).

Common resistance mechanisms by which microorganisms protect themselves from the potentially deleterious effects of their own bioactive natural products include intracellular compound modifications or sequestration, modification of the normally sensitive target so as to render it impervious to the effects of the natural product, and extracellular export (Hopwood, 2007). Within the ttn cluster one such transporter protein candidate coded for by ttnJ was found. This putative resistance protein, TtnJ, was found to have 49% identity to the cytoplasmic membrane multidrug transporter RHA1_ro04399 (YP_704343) from *Rhodococcus* sp. RHA1. It thus appears that *S. griseochromogenes* may derive TTN resistance via an export mechanism, although further studies are warranted to confirm this postulate.

C. Cloning and Biosynthesis

In certain embodiments of this invention, the TTN biosynthetic gene cluster will be introduced into a vector or vectors, which in turn is/are introduced into a host cell so as to permit recombinant production of TTN and/or analogs thereof. Methods of cloning and expressing large nucleic acids, such as gene clusters, in cells such as *Streptomyces* are well known to those of skill in the art (Stutzman-Engwall and Hutchinson, 1989; Motamedi and Hutchinson, 1987; Grim et al., 1994; Kao et al., 1994; and Hopwood et al., 1987). In some examples, nucleic acid sequences of well over 100 kb have been introduced into cells, including prokaryotic cells, using vector-based methods (see, for example, Osoegawa et al., 1998; Woon et al., 1998; Huang et al., 1996).

A wide variety of expression vectors and host cells are suitable for the synthesis of TTN or analogs thereof. The choice of vector depends on the sequence(s) that are to be expressed. Any transducible cloning vector can be used as a cloning vector for the nucleic acid constructs of this invention. However, where large clusters are to be expressed, phagemids, cosmids, P1s, YACs, BACs, PACs, HACs or similar cloning vectors can be used for cloning the nucleotide sequences into the host cell. Phagemids, cosmids, and BACs, for example, are advantageous vectors due to the ability to insert and stably propagate therein larger fragments of DNA than in M13 phage and lambda phage, respectively. Phagemids which will find use in this method generally include hybrids between plasmids and filamentous phage cloning vehicles. Cosmids which will find use in this method generally include lambda phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., 1989). The utility of employing such vectors having different marker genes may be exploited to facilitate a determination of successful transduction. In a certain embodiment, *Streptomyces* vectors are used that include sequences that allow their introduction and maintenance in *E. coli*. Such *Streptomyces/E. coli* shuttle vectors have been described (see, for example, Vara et al., 1989; Guilfoile & Hutchinson, 1991).

The gene sequences, or fragments thereof, which collectively encode the TTN gene cluster, one or more ORFs, can be inserted into expression vectors, using methods known to those of skill in the art, exemplary methods are described in publications written by Cheng et al., 2002; Tang et al., 2004; and Cheng et al., 2003, which are incorporated herein by reference. Suitable expression systems for use with the present invention include systems that function in eukaryotic and prokaryotic host cells. However, as explained above, prokaryotic systems are preferred, and in particular, systems compatible with Streptomyces spp. are of particular interest. Control elements for use in such systems include promoters, optionally containing operator sequences, and ribosome binding sites. Exemplary promoters include, but are not limited to bacterial promoters, such as those derived from sugar metabolizing enzymes, such as galactose, lactose (lac) and maltose. Additional examples include promoter sequences derived from biosynthetic enzymes such as tryptophan (trp), the beta-lactamase (bla) promoter system, bacteriophage lambda PL, and T5. In addition, synthetic promoters, such as the tac promoter (U.S. Pat. No. 4,551,433, which is incorporated herein by reference in its entirety), which do not occur in nature also function in bacterial host cells. In Streptomyces, numerous promoters have been described including constitutive promoters, such as ermE and tcmG (Shen and Hutchinson, 1994), as well as controllable promoters such as actI and actIII (Pleper et al., 1995; Pieper et al., 1995; and Wiesmann et al., 1995).

Other regulatory sequences may also be desirable which allow for regulation of expression of the replacement sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, fore example, enhancer sequences.

Selectable markers can also be included in the recombinant expression vectors. A variety of markers are know which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid. Alternatively, several polyketides are naturally colored and this characteristic provides a built-in marker for selecting cells successfully transformed by the present constructs.

Host cells for the recombinant production of TTN and its analogs can be derived from any organism with the capability of harboring a recombinant 1 nm gene cluster. Thus, the host cells of the present invention can be derived from either prokaryotic or eukaryotic organisms. Particular host cells are those constructed from the actinomycetes, a class of mycelial bacteria that are abundant producers of a number of polyketides and peptides. A particularly useful genus for use with the present system is Streptomyces. Thus, for example, S. verticillus S. ambofaciens, S. avermitilis, S. atroolivaceus, S. azureus, S. cinnamonensis, S. coelicolor, S. curacoi, S. erythraeus, S. fradiae, S. galilaeus, S. glaucescens, S. hygroscopicus, S. lividans, S. parvulus, S. peucetius, S. rimosus, S. roseofulvus, S. thermotolerans, S. violaceoruber, among others, will provide convenient host cells for the subject invention (see, e.g., Hopwood and Sherman, 1990; O'Hagan, 1991), for a description of various polyketide-producing organisms and their natural products).

Other efficient systems for gene expression in either E. coli or Streptomyces species can be used in the present invention. For example, the pET (Novagen, Inc., "pET system Mannual" $5^{th}$ Ed., 1995, Madison, Wis.) or pQE (QIAGEN, Inc. "The QIAexpressionist" $3^{rd}$ ED., 1997, Santa Clarita, Calif.). The expression efficiency in E. coli for genes from Streptomyces can be optimized by specific modification at the third positions of the first a few codons of the target gene, taking into account the biased codon usage of streptomycetes (Gramajo et al., 1991). The solubility of the overproduced proteins can be dramatically improved by either co-expression of chaperonins, such as E. coli GroEL/S (Wang et al., 2002) or the combination of low incubation temperature (as low as 17° C.), long incubation time (up to 12 hrs after induction), and low or none IPTG induction. The target gene can be expressed either as the native protein or N- or C-terminal fusion proteins. Various pET or pQE vectors for the latter are available that contain different sequences adjacent to the cloning sites. These sequences encode for a variety of peptide "tags" for detection and purification of the target protein. The peptide tags can facilitate isolation of enzymes if difficulty is encountered in the purification of the native proteins. These tags normally do not interfere with the enzyme activities and can be removed if they do become a problem.

D. Purification of TTN and Analogs Thereof

Any of a wide variety of chromatographic procedures may be employed to purify the compounds according to the present invention. For example, thin layer chromatography, gas chromatography, high performance liquid chromatography, paper chromatography, affinity chromatography or supercritical flow chromatography may be used to effect separation of various chemical species.

Partition chromatography is based on the theory that if two phases are in contact with one another, and if one or both phases constitute a solute, the solute will distribute itself between the two phases. Usually, partition chromatography employs a column, which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatograph are paper chromatograph and thin-layer chromatograph (TLC); together these are called adsorption chromatography. In both cases, the matrix contains a bound liquid. Other examples of partition chromatography are gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography.

Other methods, including crystallization, distillation, and combinations of these with chromatography can be utilized as well.

III. Methods of Treatment

In a particular aspect, the present invention provides methods for the treatment of a cancer or autoimmune disease. Treatment methods will involve administering to an individual having cancer or autoimmune disease an effective amount of a composition containing TTN or an analog thereof. An effective amount is described, generally, as that amount sufficient to detectably and repeatedly to ameliorate, reduce, minimize or limit the extent of the disease or its symptoms. More specifically, it is envisioned that the treatment with TTN or analogs thereof will kill cancer cells, inhibit their growth, and/or otherwise reverse or reduce the symptoms of the disease, and to modulate immune responses by altering the function of immune cells.

A. Cancers

Cancers that may be treated according to the present invention include cancers of the brain (glioblastomas, medulloblastoma, astrocytoma, oligodendroglioma, ependymomas), lung, liver, spleen, kidney, pancreas, small intestine, blood cells, lymph node, colon, breast, endometrium, stomach, prostate, testicle, ovary, skin, head and neck, esophagus, bone marrow, blood or other tissue. In particular, the present invention relates to the treatment of colon cancer.

B. Autoimmune Disease

An autoimmune disorder that may be treated with TTN or an analog thereof may include, but are not limited to, diabetes melitus, transplantation rejection, multiple sclerosis, premature ovarian failure, scleroderma, Sjogren's disease, systemic lupus erythematosus, vilelego, alopecia (baldness), polyglandular failure, Grave's disease, hypothyroidism, polymyositis, pemphigus, Crohn's disease, colititis, autoimmune hepatitis, hypopituitarism, myocardititis, Addison's disease, autoimmune skin diseases, uveititis, pernicious anemia, hypoparathyroidism, and/or rheumatoid arthritis.

C. Dosages

In certain embodiments, the TTN or analog thereof is administered to a subject. An effective amount of TTN or analog that may be administered to a cell includes a dose of about −0.1 µM to about 100 µM. More specifically, doses of TTN or analog to be administered are from about 0.1 µM to about 1 µM; about 1 µM to about 5 µM; about 5 µM to about 10 µM; about 10 µM to about 15 µM; about 15 µM to about 20 µM; about 20 µM to about 30 µM; about 30 µM to about 40 µM; about 40 µM to about 50 µM; about 50 µM to about 60 µM; about 60 µM to about 70 µM; about 70 µM to about 80 µM; about 80 µM to about 90 µM; and about 90 µM to about 100 µM. Of course, all of these amounts are exemplary, and any amount in-between these points is also expected to be of use in the invention.

In another embodiment of the invention, the dose range of the TTN or analogs thereof will be measured by body weight, for example, about 0.5 mg/kg body weight to about 500 mg/kg body weight. Those of skill will recognize the utility of a variety of dosage range, for example, 1 mg/kg body weight to 450 mg/kg body weight, 2 mg/kg body weight to 400 mg/kg body weighty, 3 mg/kg body weight to 350 mg/kg body weighty, 4 mg/kg body weight to 300 mg/kg body weight, 5 mg/kg body weight to 250 mg/kg body weighty, 6 mg/kg body weight to 200 mg/kg body weight, 7 mg/kg body weight to 150 mg/kg body weighty, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for TTN or analogs thereof.

The treatments may include various "unit doses." Unit dose is defined as containing a predetermined-quantity of the therapeutic composition (TTN or its analogs) calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

As is well known in the art, a specific dose level of active compounds such as TTN or analogs thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

D. Formulations and Routes for Administration

Pharmaceutical compositions of the present invention comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

E. Combined Therapy

In the context of the present invention, it is contemplated that the TTN or analogs thereof may be used in combination with an additional anti-cancer or immunotherapeutic agent to more effectively treat cancer or auto-immunity.

When an additional therapeutic agent is administered, as long as the dose of the additional therapeutic agent does not exceed previously quoted toxicity levels, the effective amounts of the additional therapeutic agent may simply be defined as that amount effective to exert a therapeutic effect when administered to an animal in combination with the TTN or analog thereof. This may be easily determined by monitoring the animal or patient and measuring those physical and biochemical parameters of health and disease that are indicative of the success of a given treatment. Such methods are routine in animal testing and clinical practice.

To kill or slow the growth of a cancer cell using the methods and compositions of the present invention, or to modulate an immune response, one can provide to the subject a TTN or analog thereof in combination with an additional therapeutic agent. These compositions would be provided in a combined amount effective to effect a therapeutic benefit (inhibition of cancer cell growth, reduction in tumor size, induction of apoptosis in a cancer cell, down-regulating of an autoimmune response, etc.). This process may involve administering TTN or analog thereof in combination with an additional therapeutic agent or factor(s) at the same time. This may be achieved by administering a single composition or pharmacological formulation that includes both agents, or by administering two distinct compositions or formulations, at the same time, wherein one composition includes TTN or analog thereof and the other includes the additional agent.

Alternatively, treatment with TTN or analog thereof may precede or follow the additional agent treatment by intervals ranging from minutes to weeks. In embodiments where the additional agent is administered separately to the patient, one would generally ensure that a significant period of time did not expire between the time of each delivery, such that the agent would still be able to exert an advantageously combined effect on the cell. In such instances, it is contemplated that one would contact the cell with both modalities within about 12-24 hr of each other and, more preferably, within about 6-12 hr of each other, with a delay time of only about 12 hr being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either TTN or analog thereof in combination with an additional therapeutic agent such as anticancer agent or immunosuppressive agent will be desired. Various combinations may be employed, where TTN or analog thereof is "A" and the additional agent is "B," as exemplified below:

A/B/A B/A/B B/B/A A/A/B B/A/A A/B/B B/B/B/A B/B/A/B
A/A/B/B A/B/A/B A/B/B/A B/B/A/A B/B/B/A B/A/A/B
B/B/B/A
A/A/A/B B/A/A/A A/B/A/A A/A/B/A A/B/B/B B/A/B/B
B/B/A/B

Agents or factors suitable for use in a combined cancer therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, one would contact a tumor or tumor cells with an agent according to the present invention along with the second agent or therapy. This may be achieved by irradiating the localized tumor site with radiation such as X-rays, UV-light, γ-rays or even microwaves. Alternatively, the tumor or tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a compound according to the present invention.

Agents that directly cross-link nucleic acids, specifically DNA, are envisaged to facilitate DNA damage leading to a synergistic, antineoplastic combination with Killin. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

5-FU has been the first-choice chemotherapy drug for colorectal cancer for many years. It is used in combination with leucovorin (a vitamin), which makes 5-FU more effective. Recently, a pill form of 5-FU has been developed, called Xeloda®, which is used for colorectal cancer that has spread to other organs. Xeloda® is also being used as neoadjuvant therapy with radiation in patients with rectal cancers to heighten the effect of radiation.

Several new chemotherapy drugs also are used for the treatment of colorectal cancer that has spread. These include Camptosar®, Eloxatin®, Avastin®, Erbitux®, and Vectibix®. Camptosar®, Eloxatin®, and Avastin® are usually given along with 5-FU for metastatic colorectal cancer. Erbitux® is administered intravenously either alone or with Camptosar®. Vectibix® is usually given in combination with 5-FU and leucovorin.

With respect to autoimmune disorders, second agents include steroids, glucocorticoids, non-steriodal anti-inflammatory drugs (NSAIDS; including COX-1 and COX-2 inhibitors), aspirin, ibuprofen, and naproxen.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

General.

IR spectra were measured on a Bruker EQUINOX 55/S FT-IR/NIR spectrophotometer (Ettlingen, DE). Optical rotations were determined on a Perkin-Elmer 241 instrument at the sodium D line (589 nm). High-resolution mass spectrometry (HRMS) analyses were acquired on an IonSpec HiRes MALDI FT mass spectrometer (Lake Forest, Calif.) for HRMALDIMS or on an Agilent 1100 series LC/MSD Trap SL for HRESIMS (Santa Clara, Calif.). NMR data were recorded on a Varian Unity Inova 400 or 500 MHz NMR spectrometer (Varian, Inc., Palo Alto, Calif.). $^1$H and $^{13}$C NMR chemical shifts were referenced to residual solvent signals: $\delta_H$ 7.26 ppm and $\delta_C$ 77.7 ppm for CDCl$_3$. $^1$H-$^1$H COSY, HMQC, HMBC, HETLOC, gHSQMBC, and gDQ-COSY were performed using either standard Varian pulse sequences or literature pulse sequences (Uhrin et al., 1998; Williamson et al., 2000). High-performance liquid chromatography (HPLC) analysis was carried out on a Varian HPLC system equipped with ProStar 210 pumps and a photodiode detector. Mobile phases used were buffer A (H$_2$O) and buffer B (CH$_3$CN). Analytical and semipreparative HPLC columns used were Alltech Alltima C18 columns, 250×4.6 mm, 5 μm and 250×10 mm, 5 respectively. Cytotoxity assays and PP inhibition assays for TTN and related analogues were performed as previously described for compound TTM and related congeners (Ju et al., 2009). Medium components and all other chemical solvents and reagents were purchased from Fisher Scientific (Fairlawn, N.J.). Silica gel 60 RP-18 (230-400 mesh, EMD Chemical Inc., Gibbstown, N.J.) was used for standard benchtop column chromatography. Amberlite XAD-16 resin was purchased from Sigma.

Bacterial Strains and Plasmids.

*Escherichia coli* DH5α was used as the host for general subcloning (Sambrook et al., 2000). *E. coli* ET12567/pUZ8002 (Paget et al., 1999) was used as the cosmid donor host for *E. coli*-Streptomyces conjugation. *E. coli* BW25113/pIJ790 and *E. coli* DH5α/pIJ773 were provided by John Innes Center (Norwich, UK) as a part of the REDIRECT Technology kit (Gust et al., 2003). The *S. griseochromogenes* wild-type strain has been described previously (Cheng et al., 1987; Cheng et al., 1990).

Biochemicals, Chemicals, and Media.

Common biochemicals and chemicals were from standard commercial sources. *E. coli* strains carrying plasmids were grown in Luria-Bertani (LB) medium with appropriate antibiotics selection (Sambrook et al., 2000). All media for *Streptomyces* growth were prepared according to standard protocols (Kieser et al., 2000). ISP-4 and tryptic soy broth (TSB) were from Difco Laboratories (Detroit, Mich.), and modified ISP-4 is ISP-4 supplemented with 0.05% yeast extract and 0.1% tryptone (Liu and Shen, 2000). ISP-4 medium and MS medium were used for *S. griseochromogenes* sporulation at 30° C. for 5-7 days.

*S. griseochromogenes* Strain Sporulation and Growth Conditions.

The *S. griseochromogenes* wild-type and LttnD and ΔttnF mutant strains SB13013 and SB13014 were grown on MS medium (consisting of autoclaved 2% mannitol, 3% soybean flour, and 1.8% agar in tap water) at 30° C. until they were well sporulated (7 days). Spores were then harvested and stored in 20% glycerol at −80° C. using previously reported standard procedures.

Plasmids and DNA Manipulation.

Plasmid extraction and DNA purification were carried out using commercial kits (Qiagen, Santa Clarita, Calif.) and genomic DNAs isolated according to literature protocol (Kieser et al., 2000). The digoxigenin-11-dUTP labeling and detection kit (Roche Diagnostics Corp., Indianapolis, Ind.) was used for preparation of DNA probes, and Southern hybridization was carried out as per manufacturer instructions.

Construction of ΔttnD and ΔttnF Mutant Strains SB13013 and SB13014.

The ttnD and ttnF genes were inactivated by application of REDIRECT Technology according to the literature protocols (Li et al., 2009; Gust et al., 2003). An apramycin (Apr) resistance gene aac(3)IV/oriT cassette was used to replace an internal region of each target gene. Mutant cosmids pBS13025 (ΔttnD) and pBS13026 (ΔttnF) for gene inactivation were constructed and then introduced into *S. griseochromogenes* by conjugation from *E. coli* ET12567/pUZ8002 according to the literature procedure with the following modifications (Li et al., 2009; Gust et al., 2003; Kieser et al., 2000). Thus, *S. griseochromogenes* spores were suspended in TSB medium and heat-shocked at 45° C. for 15 min, followed by incubation at 30° C. for 6 h. Germinated spores (as conjugation recipients) were mixed with *E. coli* ET12567/pUZ8002 harboring mutant cosmid (as conjugation donor) and spread onto modified ISP-4 plates freshly supplemented with 20 mM MgCl$_2$. After incubation at 28° C. for 16-22 h, each plate was overlaid with 1 mL of sterilized water containing Apr at a final concentration of 10 μg/mL and nalidixic acid at a final concentration of 50 μg/mL. Incubation continued at 28° C. until exconjugants appeared. The double-crossover mutants found to be apramycin resistant and kanamycin sensitive were selected, named SB13013 (ΔttnD) and SB13014 (ΔttnF), and verified by PCR and subsequently confirmed by Southern analysis.

Complementation of the ΔttnD Mutation in SB13013 and the ΔttnF Mutation in SB13014.

To construct expression plasmids for genetic complementation experiments, ttnD and ttnF were amplified and digested by NsiI and XbaI and then cloned into the same sites of pBS6027 (Li et al., 2008) to give pBS13029 (for ttnD expression) and pBS13030 (for ttnF expression). They were introduced into the corresponding mutant strains by conjugation to yield complemented strains SB13015 (i.e., SB13103/pBS13029) and SB13016 (i.e., SB13104/pBS13030), respectively.

Fermentation of *S. griseochromogenes* Wild-Type and Recombinant Strains and Production of TTN and Analogues.

A two-stage fermentation procedure was utilized to grow the *S. griseochromogenes* wild-type and recombinant strains SB13013, SB13014, SB13015, and SB13016 for TTN and analogue production as previously described (Li et al., 2009). Thus, seed medium (50 mL in a 250-mL flask) was inoculated with spores, and the flasks were incubated on a rotary shaker at 250 rpm (Innova44 Incubator Shaker Series, New Brunswick Scientific Co., Inc., Edison, N.J.) and 28° C. for 2 days. This seed culture (50 mL) was then transferred into the fermentation medium (500 mL in a 2-L flask), and the flasks were incubated on a rotary shaker at 250 rpm and 28° C. for 5 days. Both seed and production media consist of glucose 2% (separately autoclaved), soluble starch 0.5%, beef extract 0.05%, yeast extract 0.3%, soybean flour 1%, NaCl 0.1%, $K_2HPO_4$ 0.0025%, and distilled water and tap water (1:1), pH 7.0, and were sterilized by autoclaving at 121° C. for 35 min.

Extraction and Isolation of TTN (1) and Analogues 3-7 from *S. griseochromogenes* Fermentation.

The typical procedure for extraction and isolation of TTN and analogues from *S. griseochromogenes* wild-type and recombinant strain fermentation is as follows. The fermentation broth (10 L) was harvested by first bringing the broth pH to 4.0 via dropwise addition of 1 N HCl. Fermentation mixtures were then centrifuged at 3800 rpm (SLC-6000 rotor, Sorvall Evolution RC, Thermo Scientific Inc., Waltham, Mass.) at 4° C. for 20 min to pellet the mycelia. Broth supernatants were then collected and filtered to afford transparent amber-colored supernatants. Supernatants were then adsorbed onto 1.8 L of XAD-16 resin twice. Resins (now bearing secondary metabolites) were then washed with 5.4 L of distilled water to remove residual cells and broth components and then subjected to 3.6 L of acetone to elute the absorbed compounds. Acetone was removed under vacuum to give the crude products, and these products were then dissolved into 600 mL of acidic water (pH 4.0). Acidic aqueous fractions were then extracted three times with 900 mL of ethyl acetate (300 mL of fresh solvent each time). The resulting organic layers were combined and dried over anhydrous sodium sulfate. Following removal of all solids, the ethyl acetate was removed under reduced pressure to afford the crude syrups containing TTN and analogues. The syrups were then subjected to column chromatography over silica gel 60 RP-18, eluted with acetonitrile and water (from 2:8 to 9:1; 300 mL each) gradient. Each 100 mL fraction was analyzed by analytical HPLC, employing a detection wavelength of 264 nm and a linear gradient running from a buffer A/buffer B composition of 70:30 to 100% buffer B over the course of 24 min and continued at 100% buffer B for an additional 3 min, at a flow rate of 1 mL/min. Fractions containing TTN or analogues were combined and the solvents removed under reduced pressure for further purification by HPLC on an analytic or semi-preparative C-18 column. Precise purification procedures for each compound are noted below. Following collection of relevant fractions from HPLC, samples were frozen in dry ice and then solvent lyophilized for 12 h.

For purification of TTN (1) and TTN F-1 (3), semi-preparative HPLC was carried out on an Alltech Alltima C-18 column (250×10.0 mm, 5 μm), employing a linear gradient from buffer A/buffer B (70:30) to 100% buffer B over 24 min and continued at 100% buffer B for an additional 3 min, at a flow rate of 3 mL/min and monitored by UV detection at 264 nm.

For purification of TTN D-1 (4), the linear gradient went from buffer A/buffer B (90:10) to 100% buffer B over 20 min and continued at 100% buffer B for an additional 3 min, at a flow rate of 3 mL/min and monitored by UV detection at 264 nm.

For purification of diastereomers 5 and 6, an effective linear gradient involved ramping from buffer A/buffer B (60:40) to buffer A/buffer B (20:80) over 16 min with continued flow at 100% buffer detection at 264 nm. The first peak corresponded to compound 5, and the slightly slower-moving peak corresponded to compound 6. For purification of TTN D-4 (7), the linear gradient went from buffer A/buffer B (70:30) to 100% buffer B over 16 min and continued at 100% buffer B for an additional 2 min, at a flow rate of 3 mL/min and monitored by UV detection at 264 nm.

TTN F-1 (3).

Absolute yield: 16 mg from 16 L of fermentation broth of SB13014. Yellowish gum; $[\alpha]_D^{25}$=+22.9 (c 1.0, acetone); APCI-MS (positive mode) m/z 637 ([M-$H_2O$+H]$_+$, 15), 619 ([M-$2H_2O$+H]$^+$, 50), 601 ([M-$3H_2O$+H]$^+$, 15), 281 (80), 263 (100), and 139 (65); HR-ESI-MS (negative mode) m/z 653.3532 [M-H]$_-$ (calc'd for $C_{34}H_{53}O_{12}$, 653.3543, −1.6 ppm error); IR 3415, 2930, 1766, 1707, 1457, 1427, 1364, 1269, 1225, 1180, 1110, 1073, 1048, 910, 824, 794, and 706 cm$^{-1}$. For $^1H$ and $^{13}C$ NMR data, see Table 2.

TTN D-1 (4).

Absolute yield: 17 mg from 40 L of fermentation broth of SB13013. Off-yellowish gum; $[\alpha]_D^{25}$=+20.0 (c 1.0, acetone); APCI-MS (negative mode) ink 635 ([M-H]$^-$, 100); HR-MALDI-MS (positive mode) ink 659.3412 [M+Na]$^+$ (calc'd for $C_{34}H_{52}O_{11}Na$, 659.3402, 1.58 ppm error); IR 3422, 2930, 1766, 1706, 1621, 1515, 1456, 1364, 1259, 1222, 1177, 1089, 1062, 1029, 985, 907, 852, 764, and 731 cm$^{-1}$. For $^1H$ and $^{13}C$ NMR data, see Table 2.

TTN D-2 (5).

Absolute yield: 30 mg from 40 L of fermentation broth of SB13013. Off-yellowish gum; $[\alpha]_D^{25}$=+12.0 (c 2.0, acetone); APCI-MS (negative mode) m/z 651 ([M-H]$^-$, 100); HR-ESI-MS (negative mode) m/z 651.3400 [M-H]$^-$ (calc'd for $C_{34}H_{51}O_{12}$, 651.3375, 3.83 ppm error); IR 3407, 2931, 1830, 1765, 1703, 1621, 1456, 1365, 1260, 1223, 1179, 1032, 986, 957, 907, 854, and 732 cm$^{-1}$. For $^1H$ and $^{13}C$ NMR data, see Table 3.

TTN D-3 (6).

Absolute yield: 12 mg from 40 L of fermentation broth of SB13013. Off-yellowish gum; $[\alpha]_D^{25}$=+21.8 (c 1.0, acetone); APCI-MS (negative mode) m/z 651 ([M-H]$^-$, 100); HR-ESI-MS (negative mode) m/z 651.3399 [M-H]$^-$ (calc'd for $C_{34}H_{51}O_{12}$, 651.3375, 3.68 ppm error); IR 3406, 2961, 1830, 1765, 1703, 1621, 1456, 1365, 1260, 1223, 1179, 1040, 985, 956, 908, 855, and 732 cm$^{-1}$. For $^1$H- and $^{13}$C NMR data, see Table 3.

TTN D-4 (7).

Absolute yield: 4 mg from 40 L of fermentation broth of SB13013. Off-yellowish gum; $[\alpha]_D^{25}$=+12.0 (c 2.0, acetone); APCI-MS (negative mode) m/z 649 ([M-H]$^-$, 100); HR-ESI-MS (negative mode) m/z 649.3239 [M-H]$^-$ (calc'd for C$_{34}$H$_{49}$O$_{12}$, 649.3219, 3.15 ppm error); IR 3416, 2966, 1829, 1765, 1704, 1625, 1581, 1457, 1378, 1261, 1181, 1090, 1033, 986, 957, 908, and 732 cm$^{-1}$. For $^1$H and $^{13}$C NMR data, see Table 2.

TABLE 2

Summary of $^1$H and $^{13}$C NMR Data for Compounds 3, 4 and 7 in CDCl$_3$$^a$

| Position | 3 $\delta_H^b$ | $\delta_C^c$ | 4 $\delta_H^d$ | $\delta_C^c$ | 7 $\delta_H^d$ | $\delta_C^c$ |
|---|---|---|---|---|---|---|
| 1 | 1.06 (3H, t, J = 7.5) | 13.8 | 1.02 (3H, t, J = 7.6) | 13.8 | 1.10 (3H, t, J = 7.6) | 13.8 |
| 2 | 2.71 (2H, q, J = 7.5) | 21.0 | 2.67 (2H, q, J = 7.2) | 20.0 | 2.71 (2H, q, J = 7.6) | 21.2 |
| 3 |  | 141.4 |  | 139.2 |  | 153.0 |
| 4 | 5.48 (1H, t, J = 7.0) | 127.1 | 5.88 (1H, t, J = 7.2) | 143.8 | 6.34 (1H, s) | 132.0 |
| 5 | 2.10 (2H, m) | 24.7 | 2.20 (2H, m) | 26.4 |  | 201.5 |
| 6 | 1.19 (1H, m) 1.41 (1H, m) | 36.5 | 1.21 (1H, m) 1.33 (1H, m) | 37.2 | 2.28 (1H, dd, J = 15.6, 8.0) 2.50 (1H, m) | 53.0 |
| 7 | 1.58 (1H, m) | 28.9 | 1.47 (1H, m) | 30.0 | 1.50 (1H, m) | 27.4 |
| 7-CH$_3$ | 0.88 (3H, d, J = 6.5) | 20.1 | 0.83 (3H, d, J = 6.4) | 19.5 | 0.89 (3H, d, J = 6.4) | 20.2 |
| 8 | 1.20 (2H, m) | 45.3 | 1.09 (2H, m) | 45.0 | 1.15 (2H, m) | 45.0 |
| 9 | 1.54 (1H, m) | 29.6 | 1.52 (1H, m) | 30.2 | 1.50 (1H, m) | 30.0 |
| 9-CH$_3$ | 0.89 (3H, d, J = 6.5) | 20.3 | 0.86 (3H, d, J = 6.8) | 19.6 | 0.86 (3H, d, J = 6.4) | 19.5 |
| 10 | 1.44 (2H, m) | 31.3 | 1.30 (2H, m) | 33.1 | 1.30 (2H, m) | 31.7 |
| 11 | 1.58 (2H, m) | 31.2 | 1.52 (2H, m) | 32.0 | 1.40 (2H, m) | 32.4 |
| 12 | 3.82 (1H, m) | 73.6 | 3.73 (1H, m) | 74.0 | 3.73 (1H, m) | 73.7 |
| 13 | 2.70 (1H, dq, J = 8.5, 7.0) | 53.0 | 2.65 (1H, dq, J = 8.0, 7.2) | 53.0 | 2.65 (1H, dq, J = 7.8, 7.6) | 53.0 |
| 13-CH$_3$ | 1.12 (3H, d, J = 7.0) | 14.3 | 1.08 (3H, d, J = 7.2) | 13.6 | 1.08 ((3H, d, J = 7.2) | 13.8 |
| 14 |  | 215.9 |  | 215.9 |  | 215.9 |
| 15 | 2.48 (1H, dd, J = 16.5, 2.5) 2.84 (1H, dd, J = 16.5, 2.5) | 46.3 | 2.45 (1H, dd, J = 16.8, 2.8) 2.80 (1H, dd, J = 16.8, 2.8) | 46.6 | 2.45 (2H, m) | 46.5 |
| 16 | 4.39 (1H, dt, J = 10.0, 2.5) | 66.7 | 4.33 (1H, dt, J = 10.0, 2.0) | 66.8 | 4.33 (1H, dt, J = 9.6, 2.4) | 66.9 |
| 17 | 1.74 (1H, m) | 43.1 | 1.70 (1H, m) | 43.0 | 1.70 (1H, m) | 43.0 |
| 17-CH$_3$ | 0.98 (3H, d, J = 6.5) | 10.3 | 0.94 (3H, d, J = 7.2) | 10.5 | 0.94 (3H, d, J = 7.2) | 10.5 |
| 18 | 5.05 (1H, dq, J = 9.0, 6.5) | 73.7 | 5.01 (1H, dq, J = 8.0, 6.4) | 73.7 | 5.02 (1H, dq, J = 7.2, 6.4) | 73.8 |
| 18-CH$_3$ | 1.34 (3H, d, J = 6.5) | 18.6 | 1.29 (3H, d, J = 6.4) | 18.6 | 1.30 (3H, d, J = 6.4) | 18.6 |
| 1' |  | 170.3 |  | 170.3 |  | 170.3 |
| 2' | 2.93 (1H, dd, J = 16.0, 2.5) 2.84 (1H, dd, J = 16.0, 4.0) | 40.8 | 2.88 (1H, dd, J = 16.0, 8.0) 2.80 (1H, dd, J = 16.0, 4.0) | 40.9 | 2.88 (1H, dd, J = 16.0, 8.0) 2.80 (1H, dd, J = 16.0, 4.0) | 40.9 |
| 3' | 5.24 (1H, ddd, J = 9.0, 3.5, 1.0) | 64.0 | 5.20 (1H, ddd, J = 8.0, 4.0, 1.2) | 64.0 | 5.20 (1H, ddd, J = 8.8, 3.6, 1.2) | 64.1 |
| 4' |  | 142.4 |  | 142.4 |  | 142.3 |
| 5' |  | 143.3 |  | 143.3 |  | 143.3 |
| 5'-CH$_3$ | 2.13 (3H, d, J = 1.0) | 10.4 | 2.27 (3H, d, J = 1.2) | 10.3 | 2.27 (3H, d, J = 1.2) | 10.4 |
| 6' |  | 165.9 |  | 165.9 |  | 165.9 |
| 7' |  | 165.1 |  | 165.0 |  | 165.0 |
| 1" | 4.49 (1H, dd, J = 7.5, 4.5) | 71.8 | 7.28 (1H, d, J = 15.2) | 151.0 | 7.23 (1H, d, J = 16.0) | 148.8 |
| 2" | 2.60 (2H, m) | 40.5 | 5.78 (1H, d, J = 15.2) | 114.3 | 6.26 (1H, d, J = 16.0) | 122.8 |
| 3" |  | 175.4 |  | 172.3 |  | 170.4 |

$^a$Chemical shifts are reported in ppm.
Coupling constants (J) in hertz.
All signals are determined by $^1$H-$^1$H COSY, HSQC, and HMBC correlations.
$^b$$^1$H NMR, 500 MHz.
$^c$$^{13}$C NMR, 100 MHz.
$^d$$^1$H NMR, 400 MHz.

TABLE 3

Summary of $^1$H and $^{13}$C NMR Data for Compounds 5 and 6 in CDCl$_3$$^a$

| Position | 5 $\delta_H^b$ | $\delta_C^c$ | 6 $\delta_H^b$ | $\delta_C^c$ |
|---|---|---|---|---|
| 1 | 1.07 (3H, t, J = 7.2) | 13.8 | 1.05 (3H, t, J = 7.6) | 13.8 |
| 2 | 2.32 (2H, q, J = 7.2) | 20.4 | 2.30 (2H, q, J = 7.6) | 20.4 |
| 3 |  | 140.2 |  | 140.2 |
| 4 | 5.77 (1H, d, J = 8.8) | 143.3 | 5.82 (1H, d, J = 8.8) | 143.6 |
| 5 | 4.58 (1H, m) | 66.6 | 4.56 (1H, m) | 66.5 |
| 6 | 1.18, 1.47 (each 1H, m) | 45.0 | 1.10, 1.67 (each 1H, m) | 45.6 |
| 7 | 1.57 (1H, m) | 26.7 | 1.75 (1H, m) | 26.5 |
| 7-CH$_3$ | 0.89 (3H, d, J = 6.4) | 21.0 | 0.93 (3H, d, J = 6.4) | 20.3 |
| 8 | 1.08, 1.17 (EACH 1H, m) | 45.3 | 1.05, 1.16 (each 1H, m) | 44.6 |

TABLE 3-continued

Summary of $^1$H and $^{13}$C NMR Data for Compounds 5 and 6 in CDCl$_3$$^a$

| | 5 | | 6 | |
|---|---|---|---|---|
| Position | $\delta_H{}^b$ | $\delta_C{}^c$ | $\delta_H{}^b$ | $\delta_C{}^c$ |
| 9 | 1.40 (1H, m) | 32.1 | 1.55 (1H, m) | 31.4 |
| 9-CH$_3$ | 0.84 (3H, d, J = 6.4) | 19.7 | 0.84 (3H, d, J = 6.4) | 20.1 |
| 10 | 1.28 (2H, m) | 29.8 | 1.28 (2H, m) | 29.2 |
| 11 | 1.38 (2H, m) | 31.7 | 1.38 (2H, m) | 31.5 |
| 12 | 3.75 (1H, m) | 73.6 | 3.78 (1H, dt, J = 8.8, 2.4) | 73.2 |
| 13 | 2.64 (1H, dq, J = 7.6, 7.2) | 53.1 | 2.65 (1H, dq, J = 7.6, 7.2) | 52.9 |
| 13-CH$_3$ | 1.08 (3H, d, J = 7.2) | 14.2 | 1.07 (3H, d, J = 7.2) | 14.0 |
| 14 | | 215.8 | | 215.8 |
| 15 | 2.79 (1H, dd, J = 16.4, 6.0) | 46.4 | 2.79 (1H, dd, J = 16.8, 6.0) | 46.7 |
| | 2.44 (1H, dd, J = 16.4, 2.4) | | 2.46 (1H, dd, J = 16.8, 2.4) | |
| 16 | 4.35 (1H, dt, J = 9.6, 2.4) | 66.7 | 4.35 (1H, dt, J = 10.0, 2.4) | 66.7 |
| 17 | 1.70 (1H, m) | 43.1 | 1.70 (1H, m) | 43.1 |
| 17-CH$_3$ | 0.94 (3H, d, J = 6.8) | 10.4 | 0.93 (3H, d, J = 6.8) | 10.4 |
| 18 | 4.99 (1H, dq, J = 7.2, 6.0) | 73.7 | 4.98 (1H, dq, J = 7.2, 6.0) | 73.7 |
| 18-CH$_3$ | 1.29 (3H, d, J = 6.4) | 18.6 | 1.28 (3H, d, J = 6.4) | 18.6 |
| 1' | | 170.3 | | 170.2 |
| 2' | 2.88 (1H, dd, J = 16.4, 4.4) | 40.9 | 2.88 (1H, dd, J = 16.0, 4.0) | 40.9 |
| | 2.80 (1H, dd, J = 16.4, 9.2) | | 2.80 (1H, dd, J = 16.0, 8.8) | |
| 3' | 5.19 (1H, ddd, J = 7.6, 4.0, 1.2) | 63.9 | 5.19 (1H, ddd, J = 7.2, 4.0, 1.2) | 63.9 |
| 4' | | 142.4 | | 142.4 |
| 5' | | 143.1 | | 143.2 |
| 5'-CH$_3$ | 2.26 (3H, d, J = 0.8) | 10.3 | 2.26 (3H, d, J = 1.2) | 10.3 |
| 6' | | 166.0 | | 166.0 |
| 7' | | 165.1 | | 165.1 |
| 1" | 7.25 (1H, d, J = 16.0) | 149.8 | 7.24 (1H, d, J = 16.0) | 149.8 |
| 2" | 5.90 (1H, d, J = 16.0) | 117.0 | 5.89 (1H, d, J = 16.0) | 116.9 |
| 3" | | 170.9 | | 171.2 |

$^a$Chemical shifts are reported in ppm. Coupling constants (J) in hertz. All signals are determined by $^1$H-$^1$H COSY, HSQC, and HMBC correlations.
$^b$$^1$H NMR, 400 MHz.
$^c$$^{13}$C NMR, 100 MHz.

Example 2

Result

Construction and Evaluation of the ΔttnD and ΔttnF Mutant Strains SB13013 and SB13014.

To confirm the proposed function of TtnD and TtnF, in vivo gene inactivations were performed by using REDIRECT technology, as described previously (Li et al., 2009). The mutant cosmids were introduced into S. griseochromogenes by conjugation, and the resultant double-crossover mutants were confirmed by PCR and Southern blot analysis. Genetic complementations to the mutant strains were subsequently carried out to eliminate the possibility of polar effects.

Isolation and Characterization of TTN Analogue 3 from SB13014 and TTN Analogues 4-7 from SB13013.

Mutant strains SB13013 (ΔttnD) and SB13014 (ΔttnF) were fermented according to TTN production methods previously reported for the S. griseochromogenes wild-type strain, and corresponding metabolites were analyzed by HPLC with authentic TTN as a control (Li et al., 2009). Only one TTN analogue TTN F-1 was accumulated and isolated from the ΔttnF mutant strain SB13014 (FIGS. 2A-B). Its molecular formula, $C_{34}H_{54}O_{12}$, was established from the quasimolecular ion at ink 653.3532 ([M-H]$^-$), requiring an additional $CH_4O_2$ moiety relative to TTN. Instead of the C2"-C5 moiety present in the right fragment of TTN, only one trisubstituted olefin was deduced in TTN F-1 on the basis of characteristic NMR signals at $\delta_H$ 5.48 (1H, t, J) 7.0 Hz), $\delta_C$ 127.1 (d), and δC141.4 (s) (Table 2). Two substituted groups, one β-hydroxypropanoic acid moiety (C1"-C3") and one ethyl moiety (C1-C2), were observed in the 1-D and 2-D NMR data with connectivity to the carbon observed at 141.4 ppm (s, C-3) of the only double bond (Table 2). The third substituent of this double bond was assigned as a methylene group in view of the characteristic 1H NMR triplet signal observed at 5H 5.48 (1H, t, J) 7.0 Hz). This assignment was confirmed by HMQC and HMBC signals (FIG. 3A). Thus, the C5 of 3 was assigned as a methylene group and not a ketone. The upfield NMR signals were consistent with those previously observed for TTN and were assigned on the basis of 2-D NMR cross signals (Table 2 and FIG. 3A). The stereochemical configurations at C7, C9, C12, C13, C16, C17, C18, and C3' are suggested to be identical to those of 1 on the basis of their shared biosynthetic origin and the very similar optical rotations observed for TTN and TTN F-1. Although we could predict an R-configuration for C1" of TTN F-1 on the basis of bioinformatics comparisons of conserved amino acid residues of the TTN polyketide synthase KR domain and those of KR domains associated with stereochemically defined natural products (Keatinge-Clay, 2007), the absolute stereochemistry was not established experimentally. Attempts to make the Mosher ester of 3 were unsuccessful, with 3 undergoing rapid dehydration to 4 under all conditions examined (Dale et al., 1973; Ohtani et al., 1991).

Four TTN analogues, 4-7, were accumulated and isolated from the ΔttnD mutant strain SB13013 (FIGS. 2A-B). Their structures were elucidated on the basis of 1-D and 2-D NMR (including $^1$H and $^{13}$C NMR, $^1$H-$^1$H COSY, HMQC, and HMBC data), UV, IR, and HRMS data. The molecular formula of TTN D-1, $C_{34}H_{52}O_{11}$, was established from the quasi-molecular ion at m/z 659.3412 ([M+Na]$^+$), requiring one $H_2O$ less than TTN F-1. The only difference between TTN D-1 and TTN F-1 was that TTN D-1 is not a β-hydroxypropanoic acid moiety but rather an acrylic acid moiety attached to C3, as deduced from its 1-D and 2-D NMR data (Table 2). The characteristic coupling constant 15.2 Hz between the two protons at $\delta_H$ 7.28 and 5.78 (each 1H, d, J 15.2) suggests a trans-double bond within the acrylic acid moiety (Table 2). The upfield NMR signals were consistent with those of 3 and were assigned by 2-D NMR cross signals (Table 2 and FIG. 3A). Stereochemical configurations at C7, C9, C12, C13, C16, C17, C18, and C3' are predicted to be identical to those of TTN on the basis of the shared biosynthetic origin of TNN and TTN D-1.

The molecular formula of TTN D-2, $C_{34}H_{52}O_{12}$, was established from the quasi-molecular ion at m/z 651.3400 ([M-H]⁻), requiring one more oxygen atom than TTN D-1. The only difference between TTN D-2 and TTN D-1 was that the characteristic 1H NMR signal of the proton of C4 is a doublet at $\delta_H$ 5.77 (1H, d, J) 8.8 Hz), instead of the triplet signal observed in TTN F-1 and TTN D-1. Thus, C5 was assigned as a methine group instead of a methylene moiety, which is the case for 3 and 4. In view of the NMR signals at $\delta_H$ 4.58 (1H, m) and $\delta_C$ 66.6 (d), the oxygenation at C5 was deduced. C5 oxygenation was confirmed by $^1H$-$^1H$ COSY, HMQC, and HMBC cross signals (Table 3 and FIG. 3A). The upfield NMR signals were consistent with those of TTN D-1 and were assigned by 2-D NMR cross signals (Table 3 and FIG. 3A). Stereochemical configurations spanning C3' to C7 (with the exception of C5) were assigned in a fashion analogous to that used for compounds TTN and TTN F-1.

The molecular formula of TTN D-3, $C_{34}H_{52}O_{12}$, deduced on the basis of the quasi-molecular ion at m/z 651.3399 ([M-H]⁻), is identical to that of TTN D-2. The NMR spectra of TTN D-2 and TTN D-3 were almost superimposable (Table 3 and FIG. 3A). The only discernible difference between the two compounds was their $^1H$ and $^{13}C$ NMR signals around C5, suggestive of a diastereomeric relationship between 5 and 6, the result of opposite configurations at C5. The exact configuration at C5 for 5 was subsequently assigned on the basis of extensive HETLOC, gHSQMBC, and gDQCOSY experiments (Uhrin et al., 1998; Williamson et al., 2000). Thus, the anti orientation of Hh-6/H-5 was suggested by the observed large 3J value (9.0 Hz), while the gauche orientations of Hl-6/H-5, Hl-6/H-7, and Hh-6/H-7 were supported by the small 3J values. The anti orientations of Hl-6/OH and Hl-6/7-Me were shown by the small 2J value for Hl-6/C5 and the large 3J value (6.0 Hz) for Hl-6/7-Me, respectively. The gauche orientation of Hh-6/5-OH was suggested by the large 2J value (6.8 Hz) (FIG. 3B). Taken together, an S-configuration was assigned to C5 of TTN D-2, and thereby an R-configuration at C5 for TTN D-3 on the basis of their diastereomeric relationship (Table 3 and FIG. 2B).

For TTN D-4, a molecular formula of $C_{34}H_{50}O_{12}$ was established from the quasi-molecular ion at m/z 649.3219 ([M-H]−), requiring two protons less than TTN D-2. The only difference between TTN D-4 and TTN D-2 was that the characteristic $^1H$ resonance for the C4 proton in TTN D-4 was a singlet at $\delta_H$ 6.34 (1H, s), instead of a triplet as observed for TTN and TTN F-1, or a doublet as observed for TTN D-2 and TTN D-3. The suggestion, on the basis of these data, that C5 of TTN D-4 was a carbonyl carbon was prompted by the observed $^{13}C$ NMR signal at $\delta_C$ 201.5 (s), indicative of a quaternary carbon. The identity of C5 in TTN D-4 as a ketone carbon was confirmed by HMBC cross signals (Table 2 and FIG. 3A) and is the only significant structural difference between TTN D-4 and its putative methylene precursor compound TTN D-4 (FIG. 2B). The upfield NMR signals for TTN D-4 were consistent with those of TTN and its analogues and were assigned by 2-DNMR cross signals (Table 2 and FIG. 3A). Stereochemical configurations at C7, C9, C12, C13, C16, C17, C18, and C3' in TTN D-4 are likely identical to those observed in TTN on the basis of the compounds' shared biosynthetic origin.

Evaluation of PP Inhibitory Activity and Cytotoxicity of 3-7 in Comparison with 1.

Compounds 3-7 were subjected to PP inhibition and cytotoxicity assays with 1 as a control (Ju et al., 2009). Assays focused specifically on the inhibition of PP-1 and PP-2A (Table 4), while cytotoxicity assays exploited the use of selected human cancer cell lines Du145, MCF7, and HCT-115 (Table 5).

TABLE 4

Summary of in vitro Inhibition data ($1C_{50}$) in μM) for TTN and Analogues against PP-1 and PP-2

| Compound | PP-1 | PP-2A | PP-1/PP-2A |
|---|---|---|---|
| TTN (1) | 15 ± 0.8 × 10⁻³ | 0.40 ± 0.04 | 1:27 |
| TTN F-1 (3) | 0.17 ± 0.01 | 0.64 ± 0.08 | 1:3.8 |
| TTN D-1 (4) | 0.13 ± 0.02 | 0.52 ± 0.05 | 1:4 |
| TTN D-2 (5) | 9.8 ± 0.1 | 44 ± 0.1 | 1:4.5 |
| TTN D-3 (6) | 0.21 ± 0.03 | 0.80 ± 0.06 | 1:3.8 |
| TTN D-4 (7) | 028 ± 0.02 | 0.92 ± 0.04 | 1:3.3 |

TABLE 5

Summary of in vitro Cytotoxicity Data ($1C_{50}$ in μM) for TTN and Analogues against Selected Human Cancer Cell Lines

| Compound | Du145 | MCF7 | HCT-115 |
|---|---|---|---|
| TTN (1) | 5.2 ± 0.4 | 8.9 ± 0.9 | 6.8 ± 0.6 |
| TTN F-1 (3) | nd$^a$ | nd | nd |
| TTN D-1 (4) | nd | nd | nd |
| TTN D-2 (5) | nd | nd | nd |
| TTN D-3 (6) | 14 ± 3 | 11 ± 3 | 16 ± 3 |
| TTN D-4 (7) | 13 ± 4 | 17 ± 3 | 18 ± 3 |

$^a$nd no significant activity detected

Example 3

Discussion

The C2"-C5 fragment of TTN is not consistent with structural expectations for the nascent polyketide resulting from the TtnAB polyketide synthase as predicted previously (Li et al., 2009). The involvement of post-polyketide synthase steps en route to TTN was supported by the presence of four genes associated with putative tailoring enzymes: TtnC, a flavoprotein decarboxylase homologue; TtnD, a UbiD family decarboxylase homologue; TtnF, an L-carnitine dehydratase homologue; and TtnI, a putative cytochrome P450 (Li et al., 2009). On the basis of these functional assignments and the predicted synthetic capabilities of the TtnAB polyketide synthases, we have previously proposed 1 to arise through the intermediacy of a β-hydroxy acid intermediate (FIG. 4) (Li et al., 2009). Concomitant decarboxylation and dehydration to form the terminal olefin has been previously suggested (Uhrin et al., 1998; Williamson et al., 2000), and olefin installation in this manner was postulated to benefit substantially from the presence of the C5 ketone and its conjugation with the C3-C4 olefin.

The true functions of putative dehydratase TtnF and decarboxylase TtnD were evaluated using gene inactivation strategies followed by examining metabolite profiles of the resultant mutant strains. It is significant to note that under no circumstances was the previously postulated β-hydroxy acid intermediate observed, and this finding is consistent with the alternative idea that C5 oxidation proceeds after the chemistries of TtnD and TtnF (FIG. 4). The ΔttnF mutant SB13014 accumulated TTN F-1, whereas the ΔttnD mutant SB13013 accumulated compounds TTN D-1 to D-4. The accumulation of TTN F-1 in the ΔttnF mutant reveals three important details about the biosynthesis of TTN (FIGS. 2A-B). First, it confirms the functional assignment of TtnF as a dehydratase. Second, and perhaps more surprising, is that retention of the terminal acid in TTN F-1 suggests that the decarboxylase activity of TtnD requires the presence of TtnF; TtnD alone is not sufficient to effect decarboxylation. Conventional reactivity considerations dictate that dehydration of the allylic C122 in TTN F-1 or related compounds might occur upon TtnD-catalyzed decarboxylation. However, the accumulation of TTN F-1 in the presence of TtnD but the absence of TtnF reveals the flaw in this thinking, as does the fact that no trace of TTN or TTN D-1 to D-4 could be found in fermentations of the ΔttnF mutant SB13014. The biosynthetic transformations catalyzed by TtnD and TtnF appear to occur in concert. Conversely, TtnF-catalyzed dehydration of C122 is in no way dependent upon the decarboxylase activity of TtnD, as reflected by the absence of the C122 OH moiety in all compounds accumulated by the ΔttnD mutant SB13013. Third, the accumulation of TTN F1- by ΔttnF mutant SB13014 reveals that dehydration chemistry precedes polyketide C-5 oxidation needed for ketone installation. This is not the case for the ΔttnD mutant SB13013, which accumulated the C5 ketone TTN D-4 in addition to compounds TTN D1-D-3. TtnI, a cytochrome P450 homologue, the only oxygenase within the ttn cluster and a putative C5 oxidase, is likely responsible for conversion of TTN D-1 into TTN D-4. That TTN D-1 to D3, and not just TTN D-4, accumulate in SB13013 suggests that the ΔttnD mutant accumulates impaired TtnI substrates. It is clear that the activities of TtnD, TtnF, and TtnI are, to varying extents, impacted by the chemistries catalyzed by each other.

The accumulation of TTN F-1 by the ΔttnF mutant SB13014 and of TTN D1-D4 by the ΔttnD mutant SB13013 allows us to more accurately predict the biosynthesis of TTN (FIG. 4). Previous inactivation experiments indicate that TTN biosynthesis proceeds by a linear pathway (Li et al., 2009). The dialkylmaleic anhydride unit is coupled to the growing TTN polyketide intermediate prior to its release from the polyketide synthase, with the dialkylmaleic anhydride being constructed via an independent pathway that relies on TtnLMNOPRS (Li et al., 2009). Hence, the inventor envisions a biosynthetic pathway in which acetyl CoA, malonyl CoA, methylmalonyl CoA, and ethylmalonyl CoA are used by the two polyketide synthases TtnAB to produce, after TtnK-mediated dialkylmaleic anhydride coupling, TTN F-1 (FIG. 4). The absence of any C5 oxygenated analogues of TTN F-1 accumulated by the ΔttnF mutant SB13014 suggests that TtnF catalyzed chemistry precedes that of TtnI, an observation leading us now to postulate that, once formed, TTN F-1 is dehydrated by TtnF to provide diene TTN D-1 (Li et al., 2009). The findings would also be consistent with an alternative scenario wherein TtnF and TtnD act in concert to produce a diene intermediate, a substrate then for C5 oxidation by TtnI (FIG. 4). Both biosynthetic hypotheses for ultimate conversion of TTN F-1 to TTN relegate C5 oxidation to a late-stage transformation, although further inactivation efforts are warranted to determine the precise timing and coordination of the steps catalyzed by TtnF, TtnI, and TtnD. Finally, the accumulation of C5 alcohols TTN D-2 and D-3 in the ΔttnD mutant SB13013 could have resulted from C5 oxidation of compound TTN D-1 or C5 reduction of compound TTN D-4 by adventitious enzymes. However, regardless of the precise means by which TTN D-2 and TTN D-3 are produced, that both stereoisomers at C5 are observed correlates well with the production of TTN D-2 and TTN D-3 as shunt metabolites rather than intermediates formed by the stereospecific biosynthetic machinery driving production of TTN.

A critical distinction between TTN and TTM is the significantly greater selectivity of TTN for inhibition of PP-1 over PP-2A relative to TTM (Oikawa, 2002; Nishiyama et al., 1996; Sheppeck et al., 1997; takai et al., 2000). Yet surprisingly, little attention has been directed to the generation of TTN analogues able to give insight into the structural basis for this selectivity; TTN F-1 and TTN D-1 to D-4 are among the first TTN analogues reported. In light of extensive efforts to produce analogues of TTM as possible drug candidates, the lack of interest in analogue generation with TTN is truly remarkable (Oikawa, 2002; Nishiyama et al., 1996; Sheppeck et al., 1997; takai et al., 2000; Liu et al., 2003; Oikawa et al., 1997; Isobe, 1997; Oikawa et al., 1994). To investigate the impact of right hemisphere modification upon TTN bioactivity, TTN and TTN F-1 and TTN D-1 to D-4 were subjected to PP inhibition and cytotoxicity assays as previously described.$_6$ Assays focused specifically on the inhibition of PP-1 and PP-2A, while cytotoxicity assays exploited the use of selected human cancer cell lines Du145, MCF7, and HCT-115 (Ju et al., 2009). Thus, as summarized in Table 5, the impact of right hemisphere modifications on cytotoxicity appeared mixed. While the new analogues TTN F-1, TTN D-1, and TTN D-2 were inactive, TTN D-3 and TTN D-4 retained significant, albeit reduced, cytoxicity (within 3-fold of reduction relative to TTN). In contrast, modifications of the right hemisphere of TTN clearly had a profound, uniform impact on its PP-1 selectivity. As shown in Table 4, TTN potently inhibited both PP-1 and PP-2 and did so with a PP-1 selectivity of about 27-fold. Analogues TTN F-1, TTN D-1, TTN D-3 and TTN D-4 inhibited PP-1 less efficiently than TTN by approximately one order of magnitude yet inhibited PP-2A with about the same potency as TTN. In effect, any change to the C222-C5 portion of TTN led to a significant decrease in PP-1-selective inhibition, a key trademark of TTN. Not only was this the case for TTN F-1, TTN D-1, TTN D-3 and TTN D-4, but this was observed also for TTN D-2, which was a significantly poorer PP inhibitor than any other right hemisphere congener tested. PP-1 inhibition by TTN D-2 was approximately three orders of magnitude worse than that by TTN, and PP-2A inhibition by TTN D-2 was about two orders of magnitude worse than that by TTN. Hence, although the PP-1 selectivity of TTN D-2 is on par with that of all other analogues tested, the absolute inhibitory activity of TTN D-2 was markedly less than those of all the other analogues, even its diastereomer TTN D-3. The precise molecular origins of the more dramatically altered activity of TTN D-2 relative to other TTN analogues are uncertain. However, the results of these studies support proposals implicating the right hemisphere of TTN as providing much of the compound's PP-1 selectivity relative to PP-2A (Oikawa, 2002; Nishiyama et al., 1996; Sheppeck et al., 1997; takai et al., 2000).

Taken together, our ability to correlate inactivation of the ttnD and ttnF genes with specific structural modifications to TTN supports the significance of the genetic system developed for the TTN producer *S. griseochromogenes* during sequencing of the ttn biosynthetic gene cluster and reinforces current functional assignments for all genes in the ttn cluster. The accumulation of compounds TTN F-1 and TTN D-1 to D-4 in ΔttnD and ΔttnF mutant strains SB13013 and SB13014 gives significant new insight into how the C222-C5

[INSERT—IS THIS CORRECT?] fragment of TTN is produced and how these chemistries might be applied in a combinatorial biosynthetic fashion to produce new analogues of TTN. Production of TTN F-1 and TTN D-1 to D-4 has also allowed us to critically evaluate some of the structural determinants responsible for the PP-1 selectivity of TTN relative to other PP inhibitors and general cytotoxicites against selected human cancer cells. These data establish an excellent stage for future investigations of TTN biosynthesis and the future generation of TTN analogues by manipulating the TTN biosynthetic machinery.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

X. References

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 4,551,433
Bialojan and Takai, *Biochem. J.,* 256:283-290, 1988.
Bierer et al., *Proc. Natl. Acas. Sci. USA,* 87:9231-9235, 1990.
Chae et al., *Yonsei. Med. J.,* 45:978-979, 2004.
Cheng et al. *J. Antibiot.,* 43:809-819, 1990.
Cheng et al. *J. Antibiot.,* 43:890-896, 1990.
Cheng et al., *J. Antibiot.,* 40:907-909, 1987.
Cheng et al., *J. Antibiot.,* 42:141-144, 1989.
Cheng et al., *J. Bacteriol.,* 184:7013-7024, 2002.
Cheng et al., *Proc. Natl. Acad. Sci. USA,* 100(6):3149-3154, 2003.
Choi et al., *Microbiology,* 153:1095-1102, 2007.
Colby et al., *Bioorg. Med. Chem. Lett.,* 13:1601-1605, 2003.
Dai et al., *Tetrahedron Lett.,* 37:491-494, 1996.
Dale et al., *J. Am. Chem. Soc.,* 95:512-519, 1973.
Flanagan et al., *Nature,* 352:803-807, 1991.
Gramajo et al., *J. Bacteriol.,* 173:6475-6483, 1991.
Grim et al., *Gene,* 151:1-10, 1994.
Guilfoile & Hutchinson, *Proc. Natl. Acad. Sci. USA,* 88:8553-8557, 1991.
Gust et al., *Proc. Natl. Acas. Sci. USA,* 100:1541-1546, 2003.
Hong and Kahan, *Sem. Nephrol.,* 20:108-125, 2000.
Honkanen and Golden, *Curr. Med. Chem.,* 9:2055-2075, 2002.
Hopwood and Sherman, *Ann. Rev. Geneet.,* 24:37-66, 1990.
Hopwood et al., *Meth. Enzymol.,* 153:116-166, 1987.
Hopwood, *Mol. Microbiol.,* 63:937-940, 2007.
Huang et al., *Nucl. Acids Res.,* 24:4202-4209, 1996.
Hur et al., *Microbiology,* 154:2912-2919, 2008.
Ishihara et al., *Biochem. Biophys. Res. Commun.,* 159:871-877, 1989.
Isobe, Yuki, Gosei *Kagaku Kyokaishi,* 55:60-71, 1997.
Ju et al., *Org. Lett.,* 11:1639-1642, 2009.
Kao et al., *Science,* 265:509-512, 1994.
Keatinge-Clay, *Chem. Biol.,* 14:898-908, 2007.
Kelker et al., *J. Mol. Biol.,* 385:11-21, 2009.
Kieser et al., In: *Practical Streptomyces Genetics,* John Innes Foundation: Norwich, UK, 2000.
Lee et al., *Mol. Cancer Ther.,* 5:3222-3231, 2006.
Leskiw et al., *J. Bacteriol.,* 175:1995-2005, 1993.
Li and Casida, *Proc. Natl. Acas. Sci. USA,* 89:11867-11870, 1992.
Li et al., *J. Biol. Chem.,* 283:28607-28617, 2008.
Li et al., *J. Natl. Prod.,* 72:450-459, 2009.
Liu and Shen, *Antimicrob. Agents Chemothers.,* 44:382-392, 2000.
Liu et al., *Med. Chem. Lett.,* 13:1597-1600, 2003.
MacKintosh et al., *FEBS Lett.,* 264:187-192, 1990.
McCluskey et al., *J. Med. Chem.,* 45:1151-1175, 2002.
Mitsuhashi et al., *Biochem. Biophys. Res. Commun.,* 287:328-331, 2001.
Motamedi and Hutchinson, *Proc. Natl. Acad. Sci. USA,* 84:4445-4449, 1987.
Nishiyama et al., *Biosci. Biotechnol. Biochem.,* 60:103-107, 1996.
O'Hagan, In: *The Polyketide Metabolites,* Ellis Horwood Ltd., 1991.
Ohtani et al., *J. Am. Chem. Soc.,* 113:4092-4096, 1991.
Oikawa et al., *Biosci. Biotechnol. Biochem.,* 58:1933-1935, 1994.
Oikawa et al., *Tennen Yuki Kagobutsu Toronkai Koen Yoshishu,* 39:433-438, 1997.
Oikawa, *Curr. Med. Chem.,* 9:2033-2054, 2002.
Osoegawa et al., *Genomics,* 52:1-8, 1998.
Paget et al., *J. Bacteriol.,* 181:204-211, 1999.
Pieper et al., *J. Am. Chem. Soc.,* 117:11373-11374, 1995.
Pleper et al., *Nature,* 378:263-266, 1995.
Remington's Pharmaceutical Sciences, 15th Ed., 33:624-652, 1990.
Remington's Pharmaceutical Sciences, 18th Ed. Mack Printing Company, 1289-1329, 1990.
Roberge et al., *Cancer Res.,* 54:6115-6121, 1994.
Roy et al., *J. Am. Chem. Soc.,* 129, 2007.
Sakoff and McCluskey, *Curr. Pharm. Des.,* 10:1139-1159, 2004.
Sambrook et al., *Molecular cloning: a Laboratory Manual,* 3rd Ed.; Cold Spring Harbor Laboratory Press: Cold Spring Harbor, N.Y., 2000.
Sambrook et al., Molecular Cloning: A Laboratory Manual, Cold Springs Lab., New York, 1989.
Shen and Hutchinson, *J. Biol. Chem.,* 269:30726-30733, 1994.
Sheppeck et al., *J. Org. Chem.,* 62:387-398, 1997.
Shim et al., *Proc. Natl. Acas. Sci. USA,* 99:10617-10622, 2002.
Sitnikov et al., *Proc. Natl. Acas. Sci. USA,* 93:336-341, 1996.
Staunton and Weissman, *Nat. Prod. Rep.,* 18:380-416, 2001.
Stutzman-Engwall and Hutchinson, *Proc. Natl. Acad. Sci. USA,* 86:3135-3139, 1989.
Sugiyama et al., *Bioorg. Med. Chem. Lett.,* 6:3-8, 1996.
Takai et al., *Biochem. J.,* 306:657-665, 1995.
Takai et al., *Biochem. J.,* 350:81-88, 2000.
Tang et al., *Chem. Biol.,* 11:33-45, 2004.
Uhrin et al., *J. Magn. Reson.,* 130:155, 1998.
Vara et al., *J. Bacteriol.,* 171:5872-5881, 1989.
Wang et al., *Cell,* 111(7):1027-1039, 2002.

Weissman and Leadlay, *Nat. Rev. Microbiol.,* 3:925-936, 2005.
Williamson et al., *Magn. Reson. Chem.,* 38265, 2000.
Woon et al., *Genomics,* 50:306-316, 1998.

The invention claimed is:

1. An isolated analog of tautomycetin (TTN) having the formula:

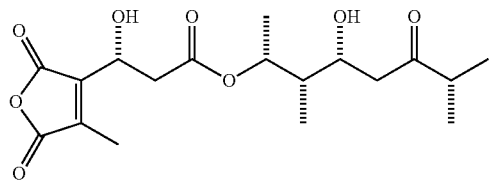

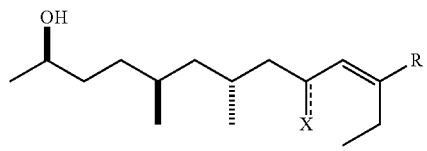

wherein X=O, OH or H, and R=(CH)$_2$COOH or CH(OH)CH$_2$-COOH.

2. The analog of claim 1, wherein the analog has the structure:

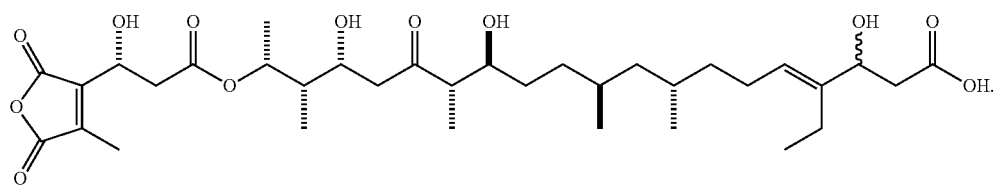 [SMILES: CC/C(=C\CC[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O)C(O)CC(=O)O]

3. The analog of claim 1, wherein the analog has the structure:

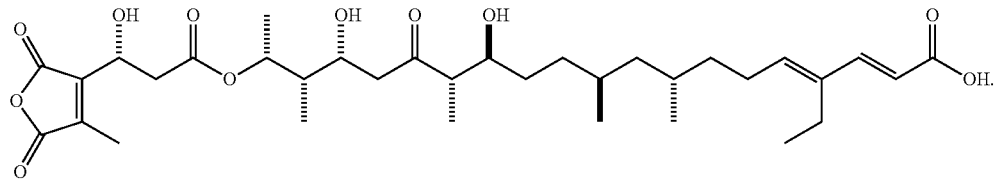 [SMILES: CCC(/C=C/C(=O)O)=C\CC[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

4. The analog of claim 1, wherein the analog has the structure:

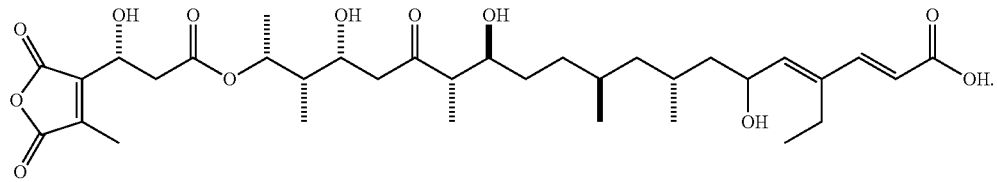 [SMILES: CCC(/C=C/C(=O)O)=C\C(O)C[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

5. The analog of claim 1, wherein the analog has the structure:

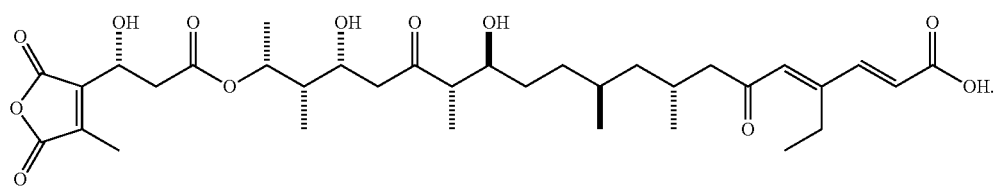 [SMILES: CCC(/C=C/C(=O)O)=C\C(=O)C[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

6. A method of producing a compound having the formula:

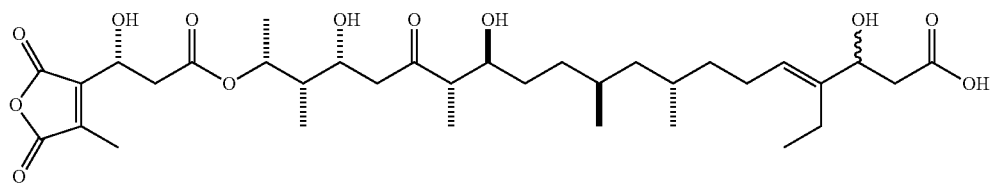 [SMILES: CC/C(=C\CC[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O)C(O)CC(=O)O]

comprising (a) providing a *Streptomyces* bacterium comprising an inactivating mutation in the ttnf gene; and (b) incubating said bacterium on conditions sufficient for a wild-type *Streptomyces* bacterium of the same species to produce tautomycetin.

7. A method of producing a compound having the formula:

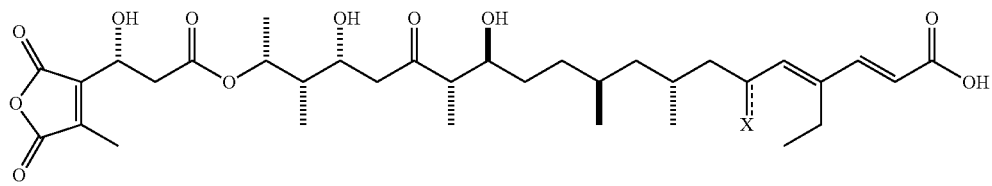

wherein X=O, OH or H, comprising (a) providing a *Streptomyces* bacterium comprising an inactivating mutation in the ttnd gene; and (b) incubating said bacterium on conditions sufficient for a wild-type *Streptomyces* bacterium of the same species to produce tautomycetin.

8. The method of claim 7, wherein the compound has the formula:

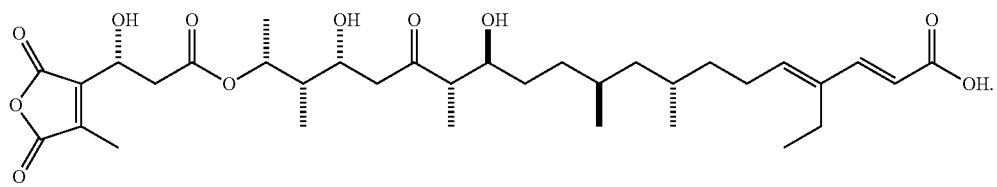 [SMILES: CCC(/C=C/C(=O)O)=C\CC[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

9. The method of claim 7, wherein the compound has the formula:

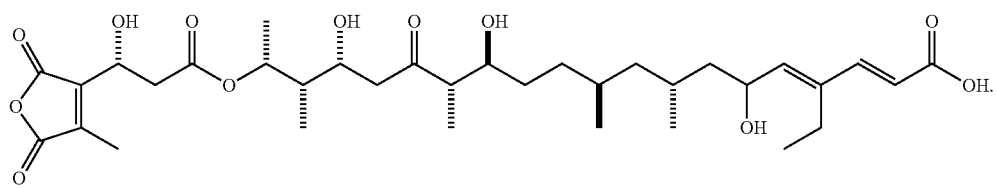 [SMILES: CCC(/C=C/C(=O)O)=C\C(O)C[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

10. The method of claim 7, wherein the compound has the formula:

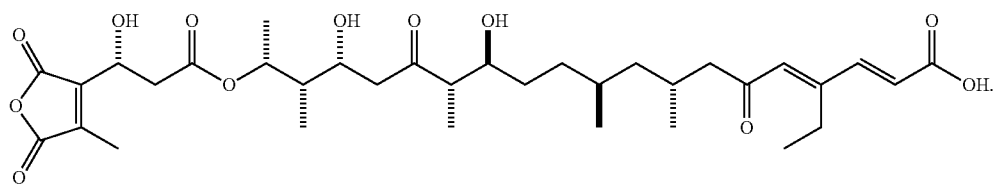 [SMILES: CCC(/C=C/C(=O)O)=C\C(=O)C[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

* * * * *

UNITED STATES PATENT AND TRADEMARK OFFICE
CERTIFICATE OF CORRECTION

PATENT NO. : 8,580,977 B2  
APPLICATION NO. : 13/101624  
DATED : November 12, 2013  
INVENTOR(S) : Shen Page 1 of 1

It is certified that error appears in the above-identified patent and that said Letters Patent is hereby corrected as shown below:

In the Claims

Claim 1, column 39, lines 8-13 and column 40, lines 2-7, delete chemical drawings and insert

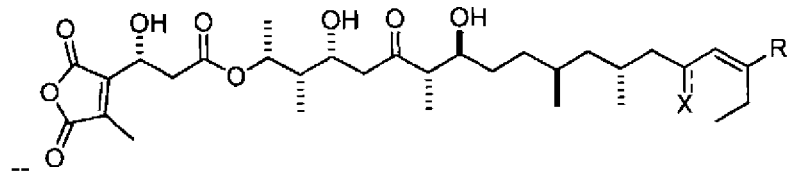

-- therefor.

Signed and Sealed this  
Fifteenth Day of April, 2014

Michelle K. Lee  
*Deputy Director of the United States Patent and Trademark Office*